(12) United States Patent
Gillen et al.

(10) Patent No.: US 8,633,237 B2
(45) Date of Patent: Jan. 21, 2014

(54) INDANE DERIVATIVES

(75) Inventors: Kevin J. Gillen, Shawlands (GB);
Jonathan Gillespie, Wishaw (GB);
Craig Jamieson, Lanarkshire (GB);
John K. F. MacLean, Kilmarnock (GB);
Elizabeth M. Moir, Edinburgh (GB);
Zoran Rankovic, Ardrie (GB)

(73) Assignee: Merck Sharp & Dohme B.V., Haarlem (NL)

( * ) Notice: Subject to any disclaimer, the term of this patent is extended or adjusted under 35 U.S.C. 154(b) by 0 days.

(21) Appl. No.: 13/262,992

(22) PCT Filed: Apr. 8, 2010

(86) PCT No.: PCT/EP2010/054634
§ 371 (c)(1),
(2), (4) Date: Apr. 26, 2012

(87) PCT Pub. No.: WO2010/115952
PCT Pub. Date: Oct. 14, 2010

(65) Prior Publication Data
US 2012/0202781 A1    Aug. 9, 2012

(30) Foreign Application Priority Data
Apr. 9, 2009   (EP) .................................... 09157744

(51) Int. Cl.
*C07D 231/18*  (2006.01)
*C07C 311/07*  (2006.01)

(52) U.S. Cl.
USPC ........ 514/407; 514/605; 548/126; 548/370.1; 564/99

(58) Field of Classification Search
None
See application file for complete search history.

(56) References Cited

FOREIGN PATENT DOCUMENTS

| | | |
|---|---|---|
| EP | 0397 044 A | 11/1990 |
| EP | 0980 864 A | 2/2000 |
| WO | WO 98/04521 | 2/1998 |
| WO | WO 02/060874 | 8/2002 |
| WO | WO 2006/015828 A | 2/2006 |
| WO | WO 2006/015829 A | 2/2006 |
| WO | WO 2009/080637 A | 7/2009 |

OTHER PUBLICATIONS

R. Soyka, et. al. "6,6-Disubstituted Hex-5-enoic Acid derivatives as Combined Thromboxane A2 Receptor Angtaongists and Synthetase Inhibitors", Journal of Medicinal Chemistry, vol. 37, No. 1, 1994, pp. 26-39.
Gross, Michael, F. , et. al."Aryl sulfonamide indane inhibitors of the KV1.5 ion channel", Bioorganic & Medicinal Chemistry Letters, vol. 17, No. 10, 2007, pp. 2849-2853.
PCT International Search Report dated May 17, 2010, mailed on Jun. 8, 2010 for related International Application No. PCT/EP2010/054634; 4 pages.
PCT Written Opinion dated May 17, 2010, mailed on Jun. 8, 2010 for related International Application No. PCT/EP2010/054634; 6 pages.

*Primary Examiner* — Kamal Saeed
(74) *Attorney, Agent, or Firm* — Susan L. Hess; John C. Todaro

(57) ABSTRACT

The present invention relates to anindane derivative according to formula I wherein the variables are defined as in the specification, or to a pharmaceutically acceptable salt or solvate thereof. The present invention also relates to a pharmaceutical composition comprising one or more of said indane derivatives and to their use in therapy, for instance in the treatment or prevention of psychiatric diseases where an enhancement of synaptic responses mediated by AMPA receptors is required, including schizophrenia, depression and Alzheimer's disease.

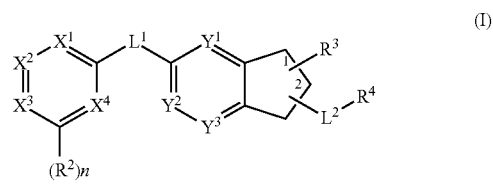

16 Claims, No Drawings

INDANE DERIVATIVES

CROSS REFERENCE TO RELATED APPLICATIONS

This application is the national stage application under 35 U.S.C. 371 of International Patent Application No.: PCT/EP2010/54634, filed in the U.S. Receiving Office on Apr. 08, 2010, which claims the benefit of European Application 09157744.5, filed Apr. 09, 2009. Each of the aforementioned PCT and EP priority applications is incorporated by reference in its entirety as if fully set forth herein.

The present invention relates to indane derivatives, to pharmaceutical compositions comprising these compounds and to their use in therapy, in particular to their use for the manufacture of a medicament for the treatment or prevention of psychiatric diseases where an enhancement of synaptic responses mediated by AMPA receptors is required.

L-glutamate is the most abundant excitatory neurotransmitter located in the mammalian central nervous system (CNS). L-glutamate plays a significant role in the control of cognition, mood and motor function and these processes are imbalanced in psychiatric and neurological disorders. The physiological effects of glutamate are mediated through two receptor families, the metabotropic (G-protein coupled) receptors and the ionotropic (ligand-gated ion channels) receptors. The ionotropic receptors are responsible for mediating the fast synaptic response to extracellular L-glutamate. The ionotropic glutamate receptors are separated into three subclasses on the basis of molecular and pharmacological differences and are named after the small molecule agonists which were originally identified to selectively activate them: AMPA (α-amino-3-hydroxy-5-methyl-4-isoxazole-propionic acid), NMDA (N-methyl-D-aspartate) and kainate (2-carboxy-3-carboxymethyl-4-isopropenylpyrrolidine). The importance of AMPA receptors in brain physiology is widely recognised and it has been shown that AMPA receptors control the majority of fast excitatory amino acid transmission in the CNS and also contribute to synaptic plasticity playing a role in a variety of physiological processes such as learning and memory. To this end there has been a growing appreciation of the utility of positive allosteric modulators of the AMPA receptor for a variety of clinical indications including schizophrenia, depression and Alzheimer's disease.

AMPA receptor subunits are encoded by four distinct genes (termed GluR1 to 4), each representing proteins of around 900 amino acids. The individual sub-units consist of a large extracellular N-terminal domain, an extracellular ligand binding site for L-glutamate formed by domains designated S1 and S2. The transmembrane domain consists of three transmembrane regions, M1, M3 and M4 together with the re-entrant loop M2. This is then followed by a long intracellular C-terminal domain. All four AMPA receptor subunits contain so-called 'flip' and 'flop' splice variants which differ in alternate slicing of 38 amino acid encoding exons (differing by less than 10 amino acids) in the S2 extracellular domain. Further heterogeneity of the AMPA receptors results from RNA editing, the most significant being the Q/R site located in the pore region (M2) of the GluR2 subunit. The R variant, which a large proportion of native GluR2 subunits are believed to comprise, is characterised by significantly reduced calcium permeability. A further R/G editing site is located in the S2 domain of GluR2, GluR3 and GluR4 with the G form exhibiting an acceleration in the kinetics of recovery from desensitisation.

The kinetics of desensitisation and deactivation are important functional properties of the AMPA receptor that control the magnitude and duration of the synaptic response to glutamate. The processes of desensitisation and deactivation can be modulated by AMPA receptor positive allosteric modulators that bind remotely from the agonist binding site, yet influence agonist binding, or indeed agonist mediated conformational changes in the receptor associated with gating and/or desensitisation. Consequently there are continued efforts to develop drugs that specifically target these properties and which will have therapeutic potential in the treatment of a wide variety of CNS disorders associated with diminished glutamatergic signalling. Examples of these conditions include age-related memory impairment, Alzheimer's Disease, Parkinson's Disease, depression, psychosis, cognitive defects associated with psychosis, attention deficit disorder and attention deficit hyperactivity disorder.

A variety of structural classes of compounds are known which act as AMPA receptor modulators (see G. Lynch, *Current Opinion in Pharmacology*, 2006, 6, 82-88 for a recent review). For example, there are the so-called benzamide compounds related to aniracetam (see A. Arai et al., *J Pharmacol Exp. Ther.*, 2002, 30, 1075-1085), the benzothiadiazine derivatives such as S-18689 (see B. Pirotte, *J Med. Chem.*, 1998, 41, 2946-2959) and the biarylpropylsulfonamide derivatives (see P. L. Ornstein et al., *J Med. Chem.* 2000, 43, 4354-4358). Another class of AMPA receptor modulators was disclosed in International Patent Appplications WO 2005/040110 and WO 2005/070916 which detail various heterocyclic compounds as being of utility as glutamate modulators. Further classes of compounds indicated to potentiate the glutamate receptor and their uses in medicine are disclosed in WO 2006/015828 and WO 2006/015829. Compounds in each of these classes exhibit varying degrees of potentiation of the AMPA receptor.

Sustained AMPA receptor activation, however, is also associated with seizures and other proconvulsant side effects (Yamada K. A., *Exp. Opin. Invest. Drugs* 2000, 9, 765-777). Consequently there remains a need for further AMPA receptor modulators which have an optimal separation between beneficial therapeutic effects and unwanted neurotoxic effects.

In a first aspect the present invention relates to an indane derivative according to formula I

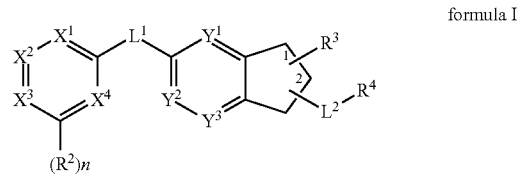

formula I wherein
$L^1$ is O, $(CR^5R^6)_m$, $OCR^7R^8$ or $CR^9R^{10}O$;
$L^2$ is $NR^{11}SO_2$ or $SO_2NR^{12}$;
$X^1$-$X^4$ are independently N or $CR^1$ with the proviso that only 1 of $X^1$-$X^4$ can be N;
$R^1$ is H, $C_{1-6}$alkyl, $C_{3-8}$cycloalkyl, $C_{1-6}$alkyloxy, halogen, CN, $SC_{1-6}$alkyl, $SOC_{1-6}$alkyl, $SO_2C_{1-6}$alkyl, $NR^{13}SO_2R^{14}$, $CH_2NR^{15}SO_2R^{16}$, $CONR^{17}R^{18}$, $NR^{19}COR^{20}$ or $SO_2NR^{21}R^{22}$, said $C_{1-6}$alkyl, $C_{3-8}$cycloalkyl and $C_{1-6}$alkyloxy being optionally substituted with one or more halogens with the proviso that each $R^1$ cannot simultaneously be H;
or two $R^1$ together form a fused 5- or 6-membered heteroaryl ring comprising 1-3 heteroatoms independently selected from O, S and N;

R² is C₁₋₆alkyl, C₃₋₈cycloalkyl, C₁₋₆alkyloxy or CN, said C₁₋₆alkyl, C₃₋₈cycloalkyl and C₁₋₆alkyloxy being substituted with one or more moiety independently selected from OH, C₁₋₆alkyloxy and NR²³R²⁴;

R³ is H, C₁₋₆alkyl, C₃₋₈cycloalkyl, C₁₋₆alkyloxy, halogen or CN, said C₁₋₆alkyl, C₃₋₈cycloalkyl and C₁₋₆alkyloxy being optionally substituted with one or more halogens;

R⁴ is H, C₁₋₆alkyl, C₂₋₆alkenyl, C₂₋₆alkynyl, C₃₋₈cycloalkyl, C₃₋₈cycloalkylC₁₋₂alkyl, NR²⁵R²⁶, C₆₋₁₀aryl or a 5-9 membered heteroaryl ring system comprising 1-3 heteroatoms independently selected from O, S and N, wherein said C₁₋₆alkyl, C₃₋₈cycloalkyl, C₆₋₁₀aryl and 5-9 membered heteroaryl ring system are optionally substituted with one or more moieties independently selected from halogen, C₁₋₆alkyl, hydroxy and C₁₋₆alkyloxy, said C₁₋₆alkyl, and C₁₋₆alkyloxy being optionally substituted with 1-3 halogens;

R⁵-R¹³ are independently H or C₁₋₆alkyl;

R¹⁴ and R¹⁶ are independently C₁₋₆alkyl;

R¹⁵, R¹⁷, R¹⁸ and R¹⁹ are independently H or C₁₋₆alkyl;

R²⁰ is C₁₋₆alkyl;

R²¹ and R²² are independently H or C₁₋₆alkyl

R²³ and R²⁴ are independently H or C₁₋₄alkyl or R²³ and R²⁴ together with the N to which they are bonded form a 4-6 membered saturated or unsaturated heterocyclic ring optionally comprising another heteroatomic moiety selected from O, S and N(R²⁷)ₚ;

R²⁵ and R²⁶ are independently H or C₁₋₄alkyl or R²⁵ and R²⁶ together with the N to which they are bonded form a 4-6 membered saturated or unsaturated heterocyclic ring optionally comprising another heteroatomic moiety selected from O, S and N(R²⁸)_q;

R²⁷ and R²⁸ are independently H or C₁₋₄alkyl;

m is 1-2;

n is 0 or 1;

p is 0 or 1;

q is 0 or 1;

Y¹-Y³ are independently N or CR²⁹ with the proviso that only 1 of Y¹-Y³ can be N;

R²⁹ is H or C₁₋₆alkyl optionally substituted with one or more halogens;

or a pharmaceutically acceptable salt or solvate thereof, with the proviso that when L¹ is (CR⁵R⁶)ₘ and L² is a substituent at the 2-position, n cannot be 0.

The term C₁₋₆alkyl, as used herein, represents a branched or unbranched alkyl group having 1-6 carbon atoms. Examples of such groups are methyl, ethyl, isopropyl, tertiary butyl and n-pentyl. Similarly the term C₁₋₄alkyl, as used herein, represents a branched or unbranched alkyl group having 1-4 carbon atoms. Examples of such groups are methyl, ethyl, isopropyl and tertiary butyl.

The term C₂₋₆alkenyl, as used herein, represents a branched or unbranched alkenyl group having 2-6 carbon atoms and at least one double bond. Examples of such groups are ethenyl and isopropenyl.

The term C₂₋₆alkynyl, as used herein, represents a branched or unbranched alkynyl group having 2-6 carbon atoms and at least one triple bond. Examples of such groups are ethynyl and propynyl.

The term C₃₋₈cycloalkyl, as used herein, represents a branched or unbranched cyclic alkyl group having 3-8 carbon atoms. Examples of such groups are cyclopropyl, cyclopentyl and 2-methylcyclohexyl.

The term C₃₋₈cycloalkylC₁₋₂alkyl, as used herein, represents a C₁₋₂alkyl group which is substituted with a C₃₋₈cycloalkyl group. Examples of such groups are cyclopropylmethyl, and 2-cyclobutylethyl.

The term C₁₋₆alkyloxy, as used herein, represents a branched or unbranched alkyloxy group having 1-6 carbon atoms. Examples of such groups are methoxy, ethoxy, isopropyloxy and tertiary butyloxy.

The term C₆₋₁₀aryl, as used herein, represents an aromatic group having 6-10 carbon atoms and comprising one ring or two rings fused together, at least one of which must be aromatic. Examples of such groups include phenyl and naphthyl.

The term SC₁₋₆alkyl, as used herein represents a thioalkyl group, for example a SCH₃ or SCH₂CH₃ group. Similarly the term SOC₁₋₆alkyl, as used herein represents an alkylsulfinyl group, for example a SOCH₃ or SOCH₂CH₃ group and the term SO₂C₁₋₆alkyl, as used herein represents an alkylsulfonyl group, for example a SO₂CH₃ or SO₂CH₂CH₃ group.

The term halogen, as used herein, represents a fluorine, chlorine, bromine or iodine.

The term solvate, as used herein, refers to a complex of variable stoichiometry formed by a solvent and a solute (in this invention, a compound of formula I). Such solvents may not interfere with the biological activity of the solute. Examples of suitable solvents include, water, ethanol and acetic acid.

Examples of 5 to 9 membered heteroaryl ring systems comprising 1-3 heteroatoms selected from O, S and N include furan, pyrrole, thiophene, imidazole, pyrrazole, thiazole, pyridine, pyrimidine, indole, indazole and benzthiophene. Similarly, examples of 5 to 6 membered heteroaryl ring systems comprising 1-3 heteroatoms selected from O, S and N include pyrrole, imidazole, pyrrazole, thiazole and pyridine.

Examples of 4 to 6 membered saturated or unsaturated heterocyclic rings optionally comprising another heteroatomic moiety selected from O, S and N(R³⁰)ₚ or 4 to 6 membered saturated or unsaturated heterocyclic rings optionally comprising another heteroatomic moiety selected from O, S and N(R³¹)_q include furan, pyrrole, thiophene, imidazole, pyrrazole, thiazole, pyridine, pyrimidine, indole, indazole, piperidine, thiopiperidine morpholine and piperazine.

In one embodiment of the present invention L¹ is O.

In another embodiment of the present invention L¹ is (CR⁵R⁶)ₘ, wherein R⁵, R⁶ and m are selected independently and have the previously defined meanings. In a further embodiment, L¹ is CH₂ or CH₂CH₂. In a further embodiment, L¹ is CH(CH₃).

In a further embodiment of the present invention L¹ is CH₂O.

In a further embodiment of the present invention L¹ is OCH₂.

In another embodiment of the present invention L² is NHSO₂ or SO₂NH. In a further embodiment, L² is N(CH₃)SO₂ or SO₂N(CH₃).

In another embodiment of the present invention, X¹-X⁴ are CR¹. In a further embodiment, one of X³ and X⁴ is N.

In another embodiment of the present invention R¹ is H, halogen, C₁₋₄alkyl, CN, C₁₋₄alkyloxy, SO₂C₁₋₆alkyl, NR¹³SO₂R¹⁴, CH₂NR¹⁵SO₂R¹⁶, or SO₂NR²¹R²² said C₁₋₄alkyl and C₁₋₄alkyloxy being optionally substituted with 1-3 halogens, wherein R¹³-R¹⁶, R²¹ and R²² have the previously defined meanings. In a further embodiment, R¹ is H, Cl, F, CF₃, OCF₃, CN, SO₂CH₃, SO₂NHCH₃, NHSO₂CH₃ or CH₂NHSO₂CH₃. In a further embodiment, R¹ is H, CF₃ or CN. In a further embodiment, R¹ is SO₂CH₃, SO₂NHCH₃, NHSO₂CH₃ or CH₂NHSO₂CH₃.

In another embodiment of the present invention R² is C₁₋₄alkyl, or C₁₋₄alkyloxy, said C₁₋₄alkyl and C₁₋₄alkyloxy being substituted with OH, C₁₋₄alkyloxy or NR²³R²⁴, wherein R²³ and R²⁴ are selected independently and have the previously defined meanings. In another embodiment, R² is methyl substituted with OH, $C_{1-4}$alkyloxy or $NR^{23}R^{24}$, wherein $R^{23}$ and $R^{24}$ are selected independently and have the previously defined meanings. In a further embodiment, $R^2$ is hydroxymethyl. In a further embodiment, $R^2$ is $C_{1-4}$alkyl substituted with amino, methylamino or dimethylamino. In a further embodiment, $R^2$ is aminomethyl, $CH_2N(CH_3)_2$, $(CH_2)_2N(CH_3)_2$ or $(CH_2)_2NH(CH_2)_2OH$.

In another embodiment of the present invention $R^3$ is H, $C_{1-6}$alkyl or $C_{1-6}$alkyloxy. In a further embodiment, $R^3$ is H, $C_{1-4}$alkyl or $C_{1-4}$alkyloxy. In a further embodiment, $R^3$ is H or methyl. In a further embodiment, $R^3$ is H.

In another embodiment of the present invention $R^4$ is H, $C_{1-6}$alkyl, $C_{3-8}$cycloalkyl, $C_{1-2}$alkyl$C_{3-8}$cycloalkyl or $NR^{25}R^{26}$, wherein said $C_{1-6}$alkyl and $C_{3-8}$cycloalkyl are optionally substituted with one or more halogens. In a further embodiment, $R^4$ is H, $C_{1-4}$alkyl, $C_{3-8}$cycloalkyl or $C_{1-2}$alkyl$C_{3-8}$cycloalkyl wherein said $C_{1-4}$alkyl and $C_{3-8}$cycloalkyl are optionally substituted with one or more halogens. In a further embodiment, $R^4$ is methyl, ethyl, isopropyl or tertiary-butyl, wherein said methyl, ethyl, isopropyl and tertiary-butyl are optionally substituted with one or more halogens. In a further embodiment, $R^4$ is cyclopropyl, cyclobutyl, cyclopentyl, cyclohexyl, cyclopropylmethyl, cyclobutylmethyl, cyclopentylmethyl or cyclohexylmethyl. In a further embodiment $R^4$ is amino, $NHCH_3$, $N(CH_3)_2$, $NHCH_2CH_3$ or $NH(CH_2CH_3)_2$. In a further embodiment, $R^4$ is piperidine, pyrrolidine, morpholine or 4-methylpiperazine. In a further embodiment, $R^4$ is ethyl, isopropyl, cyclopropyl, tertiary-butyl or dimethylamino, wherein said ethyl, isopropyl, cyclopropyl and tertiary-butyl are optionally substituted with one or more halogens.

In another embodiment of the present invention $R^4$ is $C_{6-10}$aryl or a 5-9 membered heteroaryl ring system comprising 1-2 heteroatoms independently selected from O, S and N, wherein said $C_{6-10}$aryl and 5-9 membered heteroaryl ring system are optionally substituted with one or more moieties independently selected from halogen, $C_{1-6}$alkyl, hydroxy or $C_{1-6}$alkyloxy, said $C_{1-6}$alkyl and $C_{1-6}$alkyloxy being optionally substituted with 1-3 halogens. In a further embodiment, $R^4$ is an aryl group selected from phenyl, thienyl, pyrrolyl, thiazolyl, furanyl, oxazolyl, pyridyl and pyrimidyl, said aryl group being optionally substituted with methyl, methoxy or halogen. In a further embodiment, $R^4$ is phenyl or thienyl, said phenyl or thienyl being optionally substituted with halogen, $C_{1-4}$alkyl or $C_{1-4}$alkyloxy. In a further embodiment, $R^4$ is phenyl or thienyl, said phenyl or thienyl being optionally substituted with halogen, methyl or methoxyl.

In another embodiment of the present invention, the fragment

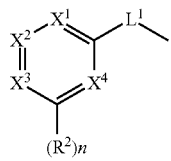

is selected from:

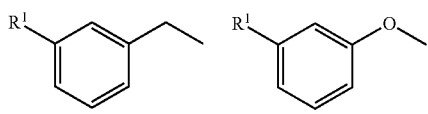

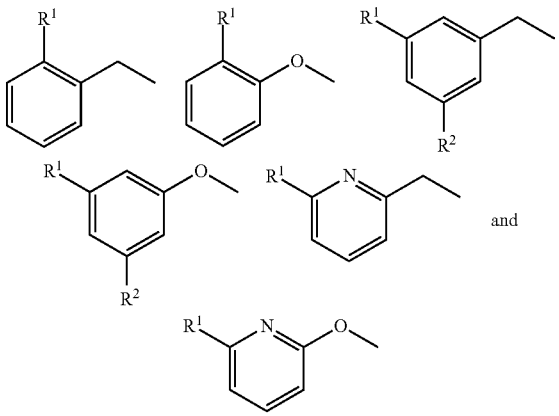

wherein $R^1$ and $R^2$ are selected independently and have the previously defined meanings.

In another embodiment of the present invention, the fragment

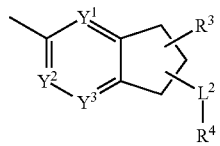

is selected from:

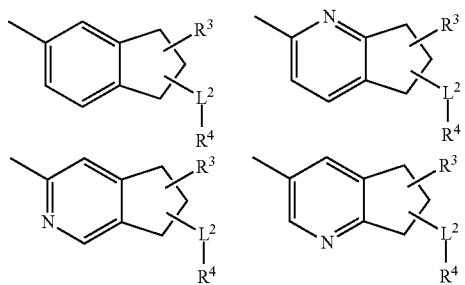

wherein $R^3$, $L^2$ and $R^4$ are selected independently and have the previously defined meanings.

In another embodiment of the present invention is an indane derivative having the formula II

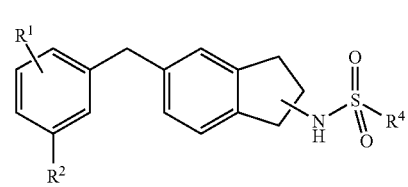

formula II wherein $R^1$, $R^2$ and $R^4$ are selected independently and have the previously defined meanings.

In a further embodiment of the present invention is an indane derivative having the general formula III

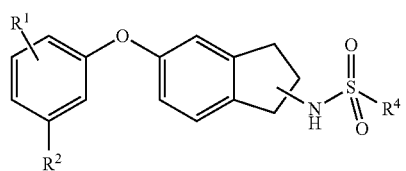
formula III
wherein R¹, R² and R⁴ are selected independently and have the previously defined meanings.
In another embodiment is an indane derivative selected from:
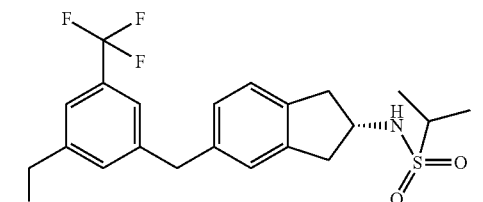
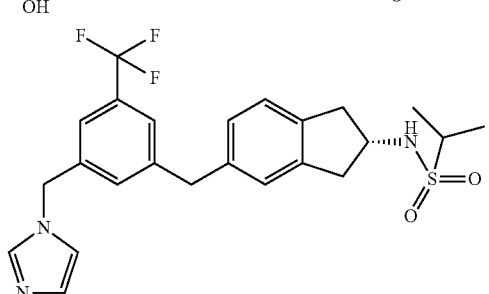
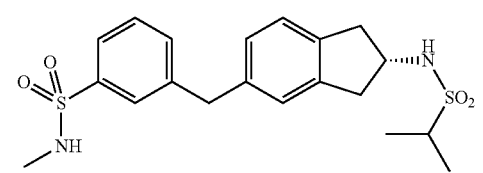
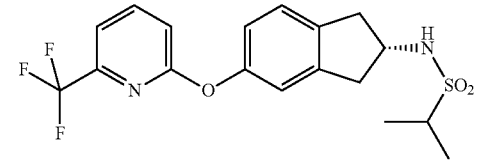
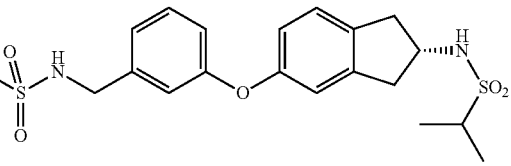
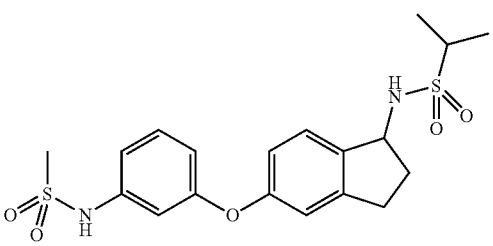
-continued
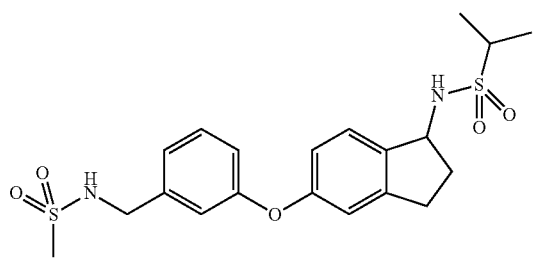
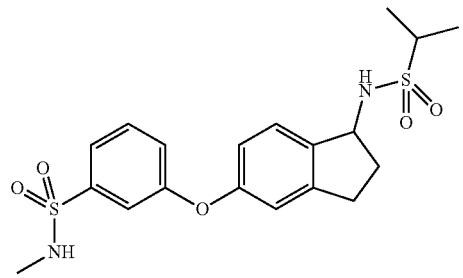
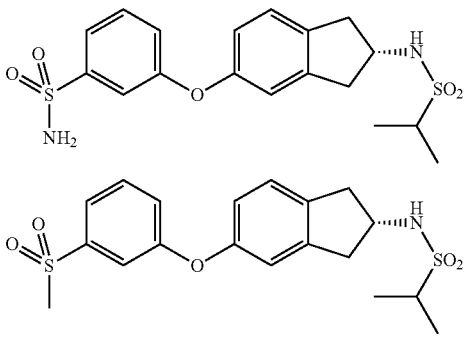
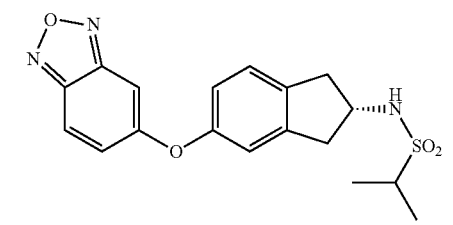
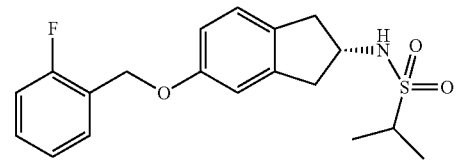
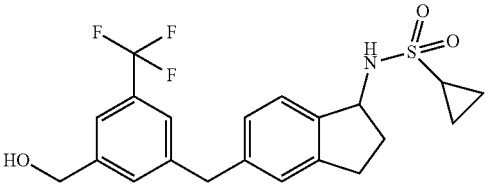
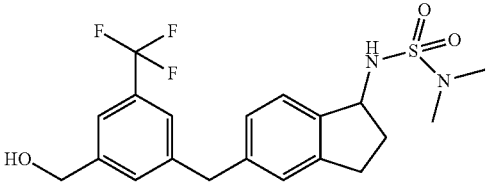

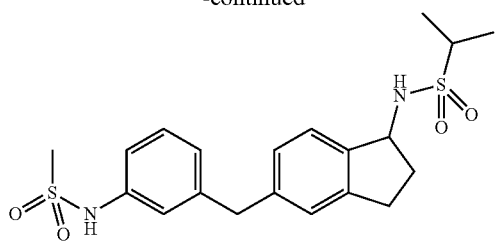

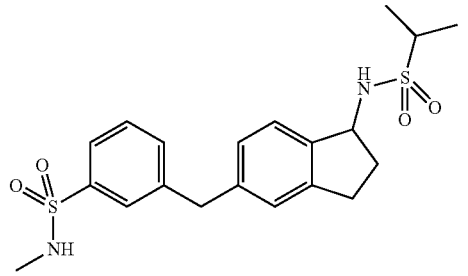

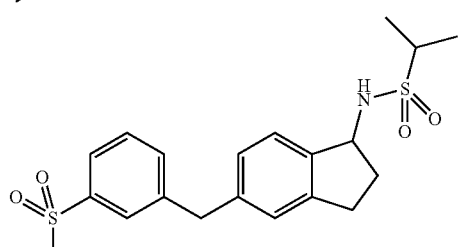

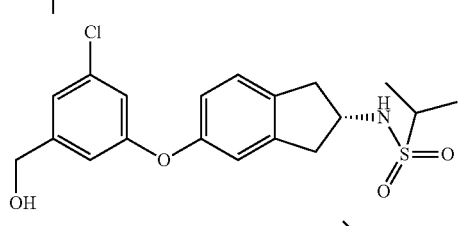

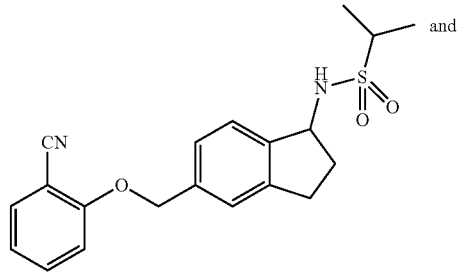

and

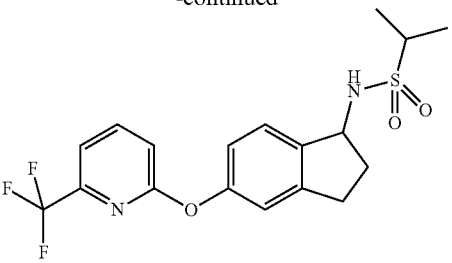

or a pharmaceutically acceptable salt or solvate thereof.

The indane derivatives of the present invention are prepared by methods well known in the art of organic chemistry. See, for example, J. March, 'Advanced Organic Chemistry' $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' $2^{nd}$ Edition, John Wiley and Sons, 1991. The protective groups are optionally removed at a convenient subsequent stage using methods well known in the art.

The synthesis of indane derivatives of formula (1) may be accomplished as outlined in Scheme 1. Thus, arylcycloalkylamines (2) may be halogenated with, for example, bromine in water, to give bromoarylcycloalkylamines (3). These in turn can be sulfonylated in the presence of a suitable organic base, such as 1,1,1-diazabicycloundecane (DBU), to give the sulphonamide (4). Subsequently functionalisation, for example, by treatment of (4) with an appropriate carbon monoxide source, such as molybdenum hexacarbonyl in, for example, methanol/acetonitrile and with the appropriate catalyst/ligand combination (using, for example, Herrmann's catalyst i.e., tri-tert-butylphosphine tetrafluoroborate as catalyst) gives the product (5), wherein $L^1$-LG is a methoxycarbonyl group.

For example, the compound (1), wherein $L^1$ is methylene can be prepared starting from the precursor (5), wherein $L^1$-LG is a methoxycarbonyl group by reduction of (5) with, for example, lithium aluminium hydride in tetrahydrofuran to give the intermediate alcohol (5, wherein $L^1$-LG is hydroxymethyl). This can then be readily chlorinated with a suitable chlorinating reagent such as thionyl chloride to provide the intermediate alkylchloride (5, wherein $L^1$-LG is chloromethyl), which in turn can be reacted with a boronic acid or ester derivative (6) in the presence of a suitable palladium catalyst and base to provide the desired adduct (1).

Scheme 1

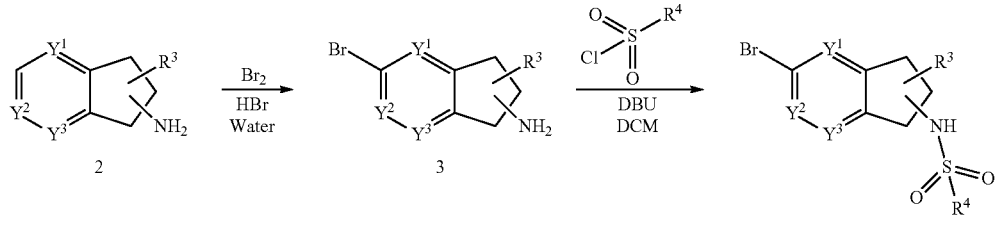

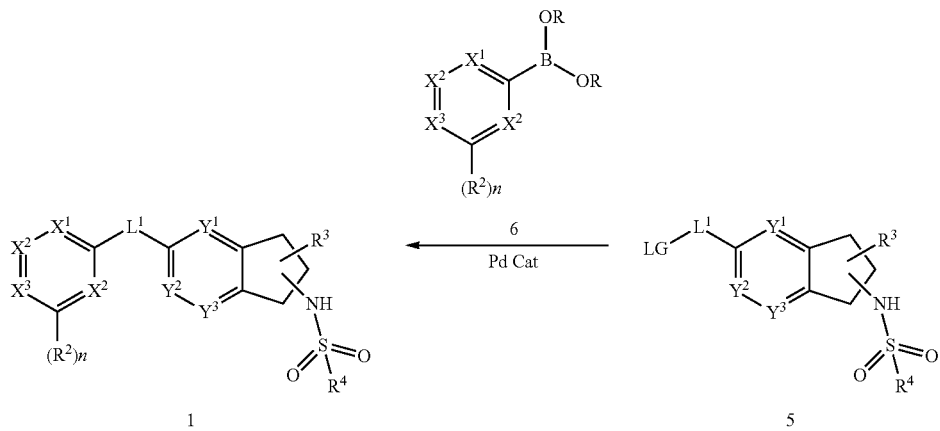

The various reagents and starting materials are either commercially available or are readily prepared using methods well known to the skilled person.

The skilled person will appreciate that the indane derivatives of formula I can alternatively be prepared using an analogous process to that of Scheme 1 but with the steps carried out in a different order. Hence, it is possible to prepare compounds of the type (11-13) as adumbrated in Scheme 2.

Scheme 2

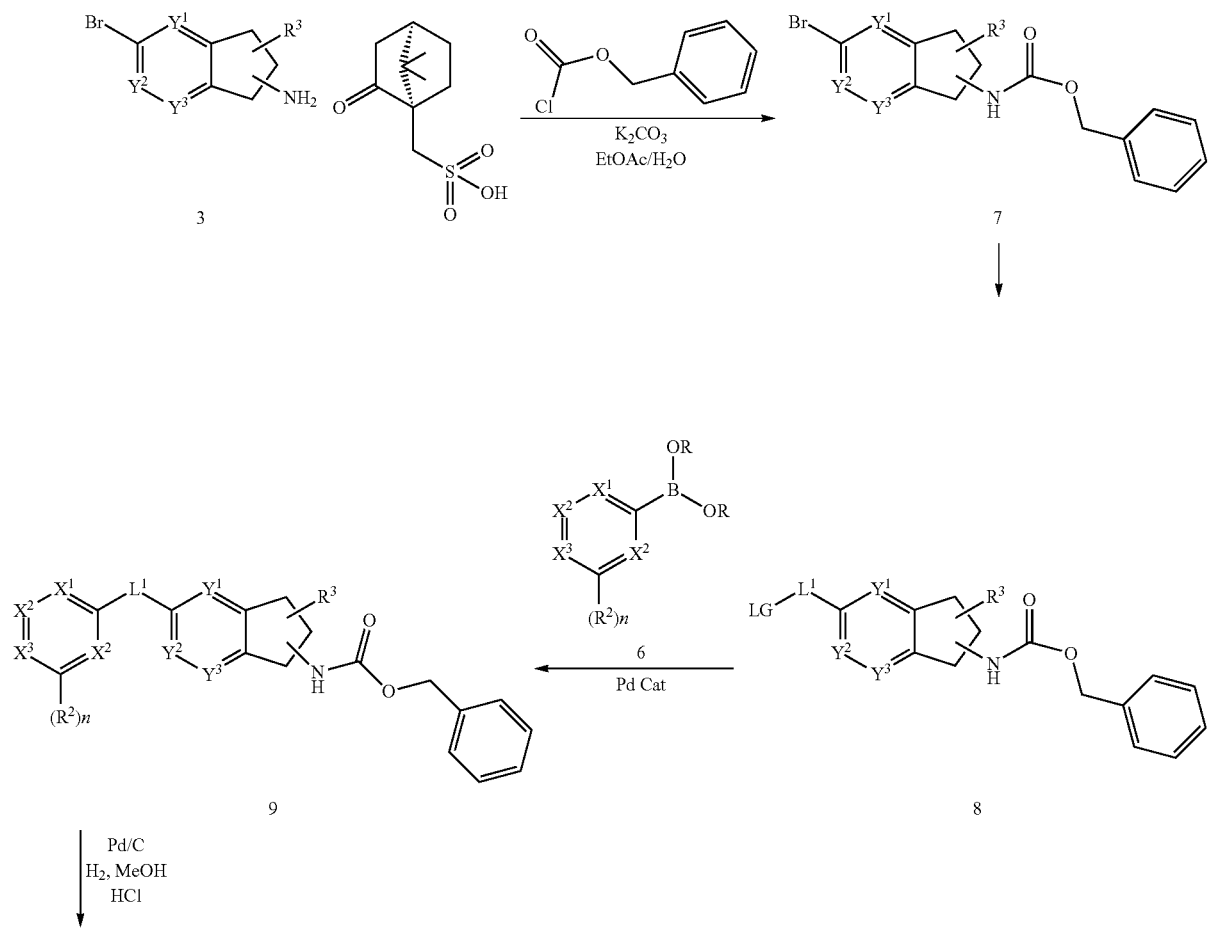

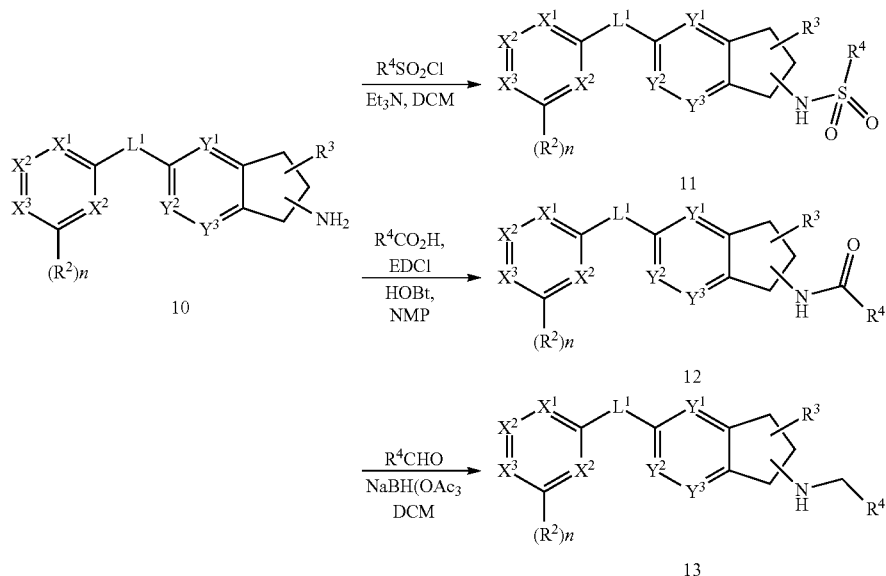

Addition of a suitable protecting group to arylcycloalkylamine derivatives such as (3) provides the carbamate (7). This can then be subsequently functionalised to provide the desired $L^1$-LG group by analogous methods to those described above in Scheme 1. Reaction with a suitably functionalised boronic acid or ester (6), again in the manner described above in Scheme 1, provides the adduct (9). Removal of the protecting group by, for example hydrogenation, yields the free amine (10), which can subsequently be derivatised using well known procedures to afford the adducts (11-13).

Other variants will also be apparent to the skilled person (Scheme 3). For example, the phenol (14) which may be prepared through reaction of (4) with bis(pinacolato)diboron in the presence of a palladium catalyst followed by oxidation with, for example, oxone, may be reacted with a boronic acid or ester (6) to produce a biaryl ether derivative (15). Similarly, (14) could be coupled with an alkyl halide derivative (16) in the presence of base to give the homologated system (17).

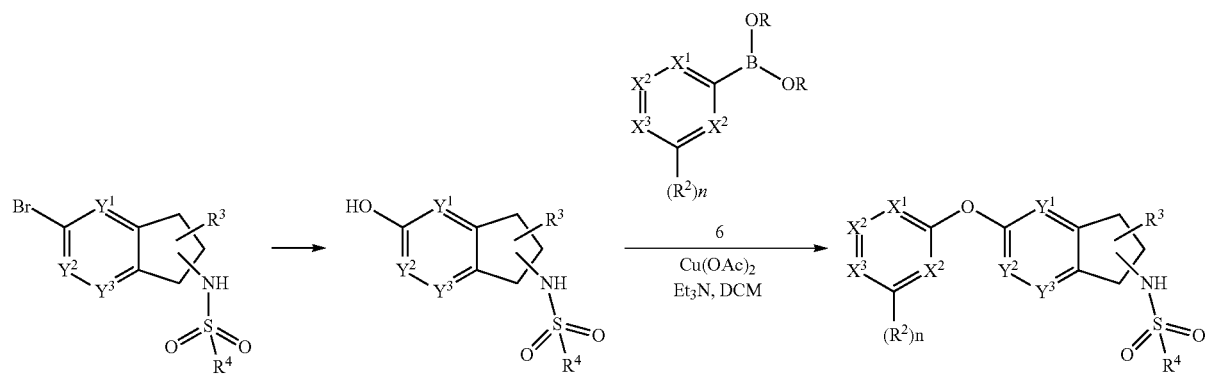

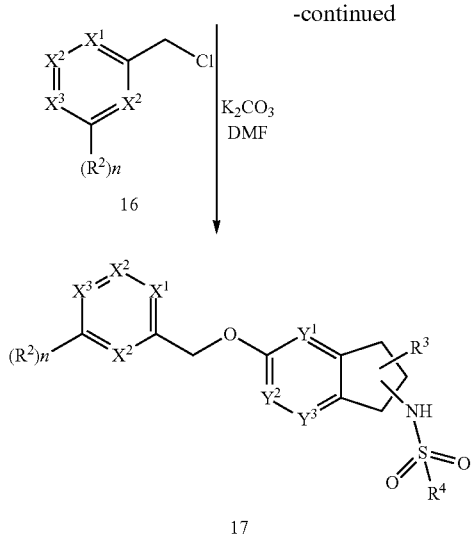

16

Alternatively with L¹-LG as chloromethyl (19), prepared as described above, the adduct (20) may be obtained upon reaction with phenol (18) under basic conditions, for example using potassium carbonate in DMF (Scheme 4).

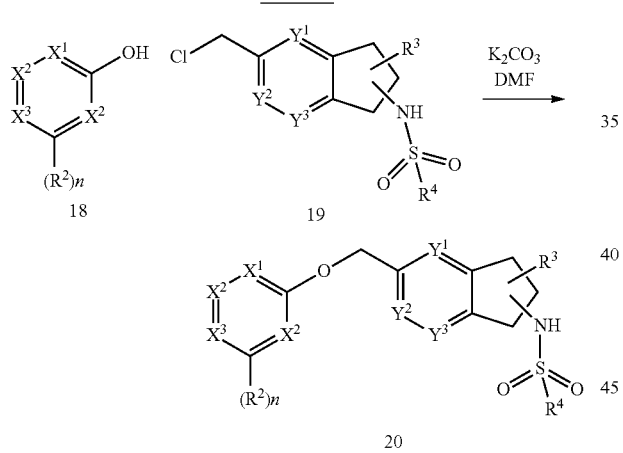

A further alternative involves reaction of the carboxylic acid (21), prepared through hydrolysis of the corresponding carboxylic acid ester described above with an aryl amine (22) to produce the amide (23) (Scheme 5).

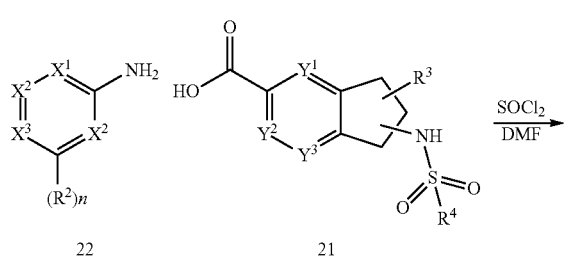

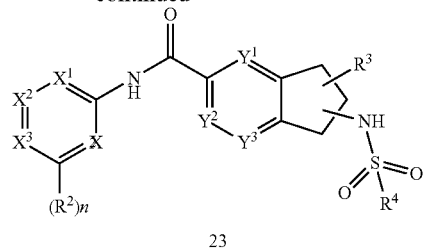

The present invention also includes within its scope all stereoisomeric forms of indane derivatives according to the present invention resulting, for example, because of configurational or geometrical isomerism. Such stereoisomeric forms are enantiomers, diastereoisomers, cis and trans isomers etc. For example, in the case where $R^2$ is 1-hydroxyethyl the compound exists as a pair of enantiomers. In the case where $R^3$ is methyl both cis and trans geometric isomers are possible. In the case of the individual stereoisomers of heterocyclic derivatives of formula I or salts or solvates thereof, the present invention includes the aforementioned stereoisomers substantially free, i.e., associated with less than 5%, preferably less than 2% and in particular less than 1% of the other stereoisomer. Mixtures of stereoisomers in any proportion, for example a racemic mixture comprising substantially equal amounts of two enantiomers are also included within the scope of the present invention.

For chiral compounds, methods for asymmetric synthesis whereby the pure stereoisomers are obtained are well known in the art, e.g., synthesis with chiral induction, synthesis starting from chiral intermediates, enantioselective enzymatic conversions, separation of stereoisomers using chromatography on chiral media. Such methods are described in *Chirality In Industry* (edited by A. N. Collins, G. N. Sheldrake and J. Crosby, 1992; John Wiley). Likewise methods for synthesis of geometrical isomers are also well known in the art.

The indane derivatives of the present invention, in the form as a free base, are isolated from reaction mixtures as pharmaceutically acceptable salts. These salts are also obtained by treatment of said free base with an organic or inorganic acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, ciric acid, benzoic acid and ascorbic acid.

The indane derivatives of the present invention also exist as amorphous forms. Multiple crystalline forms are also possible. All these physical forms are included within the scope of the present invention.

Preparation of solvates is generally known. Thus, for example, M. Caira et al, *J. Pharmaceutical Sci.*, 93 (3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5 (1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The present invention also embraces isotopically-labelled compounds of the indane derivatives described and claimed herein which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I can generally be prepared by following procedures analogous to those disclosed in the Schemes and/or in the Examples hereinbelow, by substituting an appropriate isotopically labelled reagent for a non-isotopically labelled reagent.

Prodrugs of the indane derivatives of the invention are also contemplated within the scope of the invention. A prodrug is a compound which acts as a drug precursor which, upon administration to a subject, undergoes conversion by metabolic or other chemical processes to yield a heterocyclic derivative of formula I or a solvate or salt thereof. For example, where $R^2$ is hydroxymethyl the hydroxyl group may be capped as, for example, an ester or a carbamate, which upon administration to a subject will undergo conversion back to the free hydroxyl group. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

In a further aspect, the indane derivatives of the present invention and their pharmaceutically acceptable salts and solvates are useful in therapy. As such the indane derivatives of the present invention are useful for the manufacture of a medicament for the treatment or prevention of psychiatric diseases where an enhancement of synaptic responses mediated by AMPA receptors is required. In particular the indane derivatives are useful for the manufacture of a medicament for the treatment of neurodegenerative disorders, cognitive or memory dysfunction, memory and learning disorders, attention disorder, trauma, stroke, epilepsy, Alzheimer's disease, depression, schizophrenia, psychotic disorders, anxiety, autism, a disorder or disease resulting from neurotic agents, substance abuse, alcohol psychiatric disorders, Parkinson's Disease, sleep disorders or narcolepsy or other conditions resulting from sleep deprivation. The present invention further includes an indane derivative for use in the treatment of any of the aforementioned diseases or disorders.

The present invention further includes a method for the treatment of a mammal, including a human, suffering from or liable to suffer from any of the aforementioned diseases or disorders, which comprises administering an effective amount of an indane derivative according to the present invention or a pharmaceutically acceptable salt or solvate thereof. By effective amount or therapeutically effective amount is meant an amount of compound or a composition of the present invention effective in inhibiting the above-noted diseases and thus producing the desired therapeutic, ameliorative, inhibitory or preventative effect.

The amount of an indane derivative of the present invention or a pharmaceutically acceptable salt or solvate thereof, also referred to herein as the active ingredient, which is required to achieve a therapeutic effect will, of course, vary with the particular compound, the route of administration, the age and condition of the recipient and the particular disorder or disease being treated.

A suitable daily dose for any of the above mentioned disorders will be in the range of 0.001 to 50 mg per kilogram body weight of the recipient (e.g. a human) per day, preferably in the range of 0.01 to 20 mg per kilogram body weight per day. The desired dose may be presented as multiple sub-doses administered at appropriate intervals throughout the day.

Whilst it is possible for the active ingredient to be administered alone, it is preferable to present it as a pharmaceutical composition. The present invention therefore also provides a pharmaceutical composition comprising an indane derivative according to the present invention in admixture with one or more pharmaceutically acceptable excipients, such as the ones described in Gennaro et. al., Remmington: *The Science and Practice of Pharmacy*, $20^{th}$ Edition, Lippincott, Williams and Wilkins, 2000; see especially part 5: pharmaceutical manufacturing. Suitable excipients are described e.g., in the Handbook of Pharmaceutical Excipients, $2^{nd}$ Edition; Editors A. Wade and P. J. Weller, American Pharmaceutical Association, Washington, The Pharmaceutical Press, London, 1994.

Compositions include those suitable for oral, nasal, topical (including buccal, sublingual and transdermal), parenteral (including subcutaneous, intravenous and intramuscular) or rectal administration.

The mixtures of an indane derivative according to the present invention and one or more pharmaceutically acceptable excipient or excipients may be compressed into solid dosage units, such as tablets, or be processed into capsules or suppositories. By means of pharmaceutically suitable liquids the compounds can also be applied as an injection preparation in the form of a solution, suspension, emulsion, or as a spray, e.g., a nasal or buccal spray. For making dosage units e.g., tablets, the use of conventional additives such as fillers, colorants, polymeric binders and the like is contemplated. In general, any pharmaceutically acceptable additive can be used. The indane derivatives of the invention are also suitable for use in an implant, a patch, a gel or any other preparation for immediate and/or sustained release.

Suitable fillers with which the pharmaceutical compositions can be prepared and administered include lactose, starch, cellulose and derivatives thereof, and the like, or mixtures thereof used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The present invention further includes a pharmaceutical composition, as hereinbefore described, in combination with packaging material suitable for said composition, said packaging material including instructions for the use of the composition for the use as hereinbefore described.

The invention is further illustrated by the following examples which are not intended to limit the scope thereof.

Methods

General Chemical Procedures. All reagents were either purchased from common commercial sources or synthesised according to literature procedures beginning from commercial reagents. Commercial reagents were used without further purification. Unless otherwise indicated, percent is percent by weight given the component and the total weight of the composition, temperature is in ° C. or is at ambient temperature and pressure is at or near atmospheric.

All NMR spectra were recorded using a Bruker AC400 spectrometer. Chemical shifts were recorded in parts per million using TMS as a standard. Mass spectra were recorded on a Shimadzu LC-8A (HPLC) PE Sciex API 150EX LCMS. Analytical reversed-phase LCMS analysis was carried out on LUNA C18 column (5μ; 30×4.6 mm) under gradient conditions (90% water/0.1% formic acid to 90% acetonitrile/0.1% formic acid) at a flow rate of 4 mL/min.

For chromatography eluent: x-y % solvent A in solvent B means that a gradient of the eluent of x % (v/v) of solvent A in solvent B to y Abbreviations Aq (aqueous), conc (concentrated), dimethylformamide (DMF), dichloromethane (DCM), dimethylsuphoxide (DMSO), diisopropylethylamine (DIPEA), diaza-1,5-bicyclo[4,3,0]undecane (DBU), ethyl acetate (EtoAc), high pressure liquid chromatography (HPLC), rt (room temperature), fcc (flash silica column chromatography), methanol (MeOH), mass spectroscopy (MS), tetrahydrofuran (THF).

EXAMPLE 1

(S)-N-(5-(3-(hydroxymethyl)-5-(trifluoromethyl) benzyl)-2,3-dihydro-1H-inden-2-yl)propane-2-sulfonamide a) 5-bromo-2,3-dihydro-1H-inden-2-amine Hydrobromide

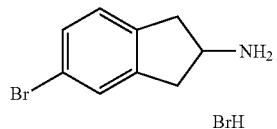 [SMILES: NC1Cc2ccc(Br)cc2C1 ; Br]

A suspension of aminoidane hydrochloride (150 mmol, 25.43 g) and water (127 mL) under $N_2$ was heated to an internal temp of 58-60° C. in an oil bath and to the resulting solution was added bromine (154 mmol, 7.93 mL, 24.67 g) dropwise over approx 40 min maintaining internal temperature around 58-60° C. The reaction mixture was stirred at 60° C. for a further 1 h then 48% HBr (22.91 mL) was added over 2 minutes and mixture stirred for 10 min. The reaction was then cooled to room temperature over 1 h and stood at room temperature overnight. The resulting solids were isolated by filtration and washed with 2-propanol (2×20 mL) to give a beige solid. This was collected by filtration and re-crystallised from hot water to give 5-bromo-2,3-dihydro-1H-inden-2-amine hydrobromide as a beige solid (20 g) A second crop was (4.5 g) was obtained in a similar way. (24.5 g, 55.8%). $^1$H NMR (400 MHz, DMSO$_{d6}$) δ 3.03 (m, 2H) 3.43 (m, 2H) 4.13 (m, 1H) 7.22 (d, 1H) 7.37 (d, 1H) 7.46 (s, 1H)

b) (S)-5-bromo-2,3-dihydro-1H-inden-2-amine((1R, 4S)-7,7-dimethyl-2-oxobicyclo[2.2.1]heptan-1-yl) methanesulfonate

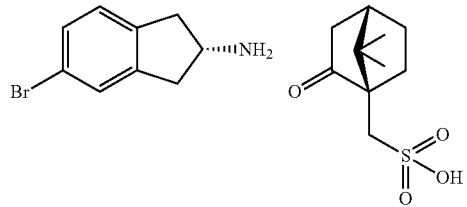

To a suspension of 5-bromo-2,3-dihydro-1H-inden-2-amine hydrobromide (107 mmol, 31.27 g) and N-methylmorpholine (112 mmol, 12.32 mL, 11.33 g) in methanol (66.6 mL) was heated to 58-62° C. and a solution of ((1R,4S)-7,7-dimethyl-2-oxobicyclo[2.2.1]heptan-1-yl)methanesulfonic acid (107 mmol, 24.79 g) in methanol (53.4 mL) was added over 3 min maintaining internal temp at 60-65° C. The addition funnel was rinsed with MeOH (13.3 mL) and rinsings added to reaction. The mixture was stirred at 60-65° C. for 10 min until a clear solution was obtained. The reaction was then allowed to cool to room temperature and stirred for a total of 4 h. The solids were collected by filtration and washed with a pre-cooled mixture of isopropyl acetate/methanol 2:1 (2×15 mL) followed by water (2×15 mL). The crude product was dried in a vacuum oven at 50° C. overnight to yield (18.03 g) of a fluffy white solid. This was suspended in methanol (130 mL) and heated to reflux for 4 h then allowed to cool to room temperature with stirring over 2 h and stirring continued at room temperature for a further 1 h. Solids were then isolated by filtration and washed with a pre-cooled solution of isopropylacetate/methanol (2:1, 2×18 mL). The colourless solid (13.82 g) was dried in the vacuum oven for 60 h. Refluxing in methanol followed by washing the solid with isopropyl acetate/methanol was repeated until the desired enantiomeric ratio was obtained. (S)-5-bromo-2,3-dihydro-1H-inden-2-amine ((1S,4R)-7,7-dimethyl-2-oxobicyclo[2.2.1]heptan-1-yl)methanesulfonate was obtained as a colourless solid (12.28 g, e.e. 100:0, 25.9%).

$^1$H NMR (400 MHz, DMSO$_{d6}$) δ 0.74 (s, 3H) 1.05 (s, 3H) 1.28 (m, 2H) 1.80 (m, 2H) 1.94 (m, 1H) 2.25 (m, 1H) 2.38 (m, 1H) 2.69 (m, 1H) 2.83-2.95 (m, 3H) 3.25 (m, integration masked water peak) 4.02 (m, 1H) 7.25 (d, 1H) 7.39 (d, 1H) 7.50 (s, 1H) 8.00 (bs, 3H)

c) (S)-N-(5-bromo-2,3-dihydro-1H-inden-2-yl)propane-2-sulfonamide

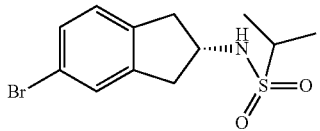 [SMILES: CC(C)S(=O)(=O)N[C@H]1Cc2ccc(Br)cc2C1]

(S)-5-bromo-2,3-dihydro-1H-inden-2-amine((1R,4S)-7,7-dimethyl-2-oxobicyclo[2.2.1]heptan-1-yl)methanesulfonate (3.38 mmol, 1.5 g) was suspended in dichloromethane (20 mL) and DBU (10.13 mmol, 1.513 mL, 1.542 g) added. The mixture was purged with nitrogen and cooled in an ice bath before drop-wise addition of propane-2-sulfonyl chloride (6.75 mmol, 0.754 mL, 0.963 g). Stirring was continued at 0° C. for 1 h before allowing to come to room temperature. The mixture was diluted with DCM (100 mL) and 1N HCl (100 mL) and the phases mixed and separated. The aqueous phase was further extracted with DCM (2×100 mL) before combined organics were washed with brine. Concentration gave ~1.5 g of a light yellow oil which was purified on 20 g Si eluting with 75% Dichloromethane/Heptane then neat DCM. Desired fractions were collected and concentrated to give (S)-N-(5-bromo-2,3-dihydro-1H-inden-2-yl)propane-2-sulfonamide as a colourless oil (1.0 g, 93%). $^1$H NMR (400 MHz, CDCl$_3$) δ 1.39 (d, 6H) 2.88 (m, 2H) 3.18 (sept, 1H) 3.28 (m, 2H) 4.27 (m, 1H) 4.40 (m, 1H) 7.08 (d, 1H) 7.30 (d, 1H) 7.35 (s, 1H)

d) (S)-methyl 2-(1-methylethylsulfonamido)-2,3-dihydro-1H-indene-5-carboxylate

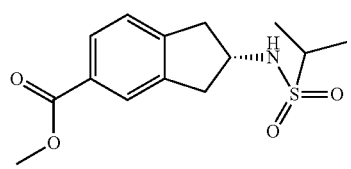 [SMILES: COC(=O)c1ccc2c(c1)C[C@@H](NS(=O)(=O)C(C)C)C2]

(S)-N-(5-bromo-2,3-dihydro-1H-inden-2-yl)propane-2-sulfonamide, (1.25 mmol, 0.4 g), DBU (1.88 mmol, 0.281 mL, 0.286 g), acetoxy(2-(dio-tolylphosphino)benzyl)palladium (0.125 mmol, 0.118 g), tri-tert-butylphosphine tetrafluoroborate (0.251 mmol, 0.072 g) and molybdenum hexacarbonyl (1.25 mmol, 0.331 g) were added to a Smith Creator microwave vial and heated at 150° C. for 30 min. The mixture was concentrated before dissolving in dichloromethane and filtration through a dicalite plug. Purification was achieved on silica eluting with DCM to give (S)-methyl 2-(1-methylethylsulfonamido)-2,3-dihydro-1H-indene-5-carboxylate as a brown oil (0.327 g, 88%). $^1$H NMR (400 MHz, CDCl$_3$) δ 1.38 (d, 6H) 2.95 (d, 2H) 3.18 (sept, 1H) 3.36 (m, 2H) 3.90 (s, 3H) 4.3 (m, 2H) 7.26 (d, 1H) 7.87 (m, 2H)

e) (S)-N-(5-(hydroxymethyl)-2,3-dihydro-1H-inden-2-yl)propane-2-sulfonamide

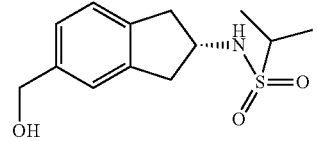

(S)-methyl-2-(1-methylethylsulfonamido)-2,3-dihydro-1H-indene-5-carboxylate (2.502 mmol, 744 mg) was dissolved in dry THF (20 mL) and was purged with nitrogen and cooled in an ice bath. Lithium aluminium hydride (7.51 mmol, 7.51 mL) was added dropwise and stirring continued at 0° C. for 10 min. The mixture was quenched by addition of methanol followed by 1:1 THF/water and 1N HCl before concentration to remove organics. The residue was partitioned between dichlormethane/1N HCl. and the phases mixed and separated. The aqueous layer was further extracted with DCM (×2) Combined organics washed with brine and concentrated before purification on silica eluting with 2% MeOH/DCM to give (S)-N-(5-(hydroxymethyl)-2,3-dihydro-1H-inden-2-yl)propane-2-sulfonamide (0.692 g, 103%). $^1$H NMR (400 MHz, CDCl$_3$) δ 1.39 (d, 6H) 1.71 (bt, 1H) 2.89 (m, 2H) 3.18 (sept, 1H) 3.30 (m, 2H) 4.28 (m, 1H) 4.41 (m, 1H) 4.66 (d, 2H) 7.18 (m, 2H) 7.24 (m, 1H)

f) (S)-N-(5-(chloromethyl)-2,3-dihydro-1H-inden-2-yl)propane-2-sulfonamide

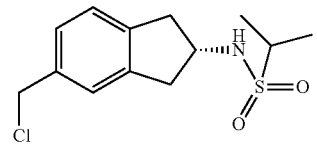 [SMILES: CC(C)S(=O)(=O)N[C@H]1Cc2ccc(CCl)cc2C1]

(S)-N-(5-(hydroxymethyl)-2,3-dihydro-1H-inden-2-yl) propane-2-sulfonamide (2.57 mmol, 692 mg) was dissolved in DCM (10 mL), thionyl chloride (5.14 mmol, 0.373 mL, 611 mg) added and the solution stirred at room temperature. After 45 min the mixture was concentrated then azeotroped with dichloromethane (4×10 mL) to give a yellow oil. This was used immediately in step f.

g) (S)-methyl 3-((2-(1-methylethylsulfonamido)-2,3-dihydro-1H-inden-5-yl)methyl)-5-(trifluoromethyl)benzoate

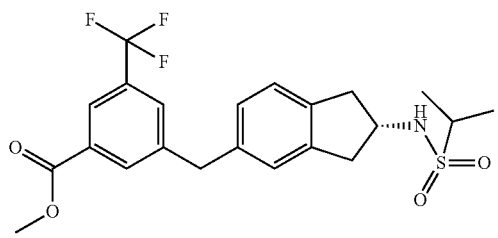 [SMILES: COC(=O)c1cc(Cc2ccc3c(c2)C[C@@H](NS(=O)(=O)C(C)C)C3)cc(C(F)(F)F)c1]

To (S)-N-(5-(chloromethyl)-2,3-dihydro-1H-inden-2-yl)propane-2-sulfonamide (0.160 mmol, 46 mg) in THF (1 mL) was added methyl 3-(5,5-dimethyl-1,3,2-dioxaborinan-2-yl)-5-(trifluoromethyl)benzoate (0.160 mmol, 50.5 mg), Bromo(N-succinimidyl)bis-(triphenylphosphine)palladium(II) (7.99 µmol, 6.46 mg) and sodium carbonate (1.000 mmol, 0.5 mL). The reaction was heated to 100° C. for 10 minutes by microwave irradiation before diluting with DCM and filtering through a hydrophobic frit. The solvent was removed in vacuo before redissolving in MeCN (500 µL) and purifying by reverse phase preparative chromatography to give (S)-methyl 3-((2-(1-methylethylsulfonamido)-2,3-dihydro-1H-inden-5-yl)methyl)-5-(trifluoromethyl)benzoate (23.2 mg, 31.9%). MS (ESI): m/z [M+H]+ 456.0 h) (S)-N-(5-(3-(hydroxymethyl)-5-(trifluoromethyl)benzyl)-2,3-dihydro-1H-inden-2-yl) propane-2-sulfonamide

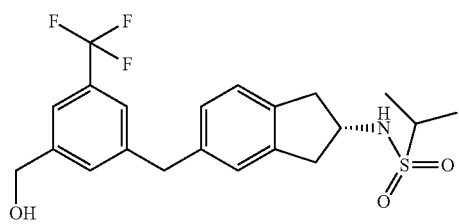 [SMILES: CC(C)S(=O)(=O)N[C@H]1Cc2ccc(Cc3cc(CO)cc(C(F)(F)F)c3)cc2C1]

To (S)-methyl 3-((2-(1-methylethylsulfonamido)-2,3-dihydro-1H-inden-5-yl)methyl)-5-(trifluoromethyl)benzoate (0.044 mmol, 20 mg) at 0° C. in THF (1 mL) under an argon atmosphere was added Lithium aluminium hydride in THF (0.044 mmol, 0.044 mL) dropwise. The reaction was left to stir for 1.5 hrs at 0° C. The reaction was quenched with water before the addition of 5N HCl (aq) to adjust the pH to 5. The mixture was filtered through a celite cartridge before washing with EtOAc. The EtOAc layer was washed with water (×1) before drying the EtOAc over MgSO4. The solvent was removed in vacuo before purifying the crude (1:1 EtOAc/Heptane, 4 g silica cartridge) to give the title compound (7.5 mg, 40%). MS (ESI): m/z [M+Na]+ 450.0

EXAMPLE 2

(S)-N-(5-(3-chloro-5-(hydroxymethyl)benzyl)-2,3-dihydro-1H-inden-2-yl)propane-2-sulfonamide

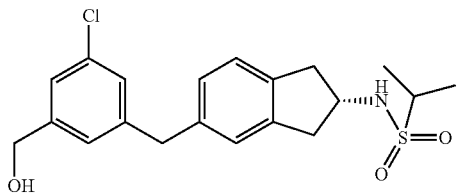 [SMILES: CC(C)S(=O)(=O)N[C@H]1Cc2ccc(Cc3cc(Cl)cc(CO)c3)cc2C1]

A mixture of 3-chloro-5-(methoxycarbonyl)phenylboronic acid (0.320 mmol, 68.5 mg), (S)-N-(5-(chloromethyl)-2,3-dihydro-1H-inden-2-yl)propane-2-sulfonamide (0.320 mmol, 92 mg), and transPdBr(N-succ)(PPh3)2 (0.016 mmol, 12.96 mg) in THF (5 mL). 2.5 mL of 2M aq Na2CO3 was added and the reaction mixture heated at 65° C. for 5 hrs, then allowed to stand overnight. Water was added and the reaction mixture extracted with EtOAc (×3). The combined EtOAc layers were washed with brine, dried over MgSO4, filtered and the solvent removed to give 117 mg of crude intermediate ester. Purification by flash column chromatography-silica gel (1:4 EtOAc:Heptane) gave 46 mg intermediate ester. This was dissolved in THF (5 mL). Sodium borohydride (0.639 mmol, 24.19 mg) was added and the reaction mixture stirred at room temp for 6 hrs, then allowed to stand overnight. MeOH was added and the reaction mixture stirred at room temp for 30 mins then concentrated to dryness. Water was added followed by DCM and the whole was then filtered through a hydrophobic frit. The DCM layer was concentrated to dryness and purification by reverse phase HPLC gave desired product (19.1 mg, 15.7%). MS (ESI): m/z [M−H]− 392.2

EXAMPLE 3

(S)-N-(5-(3-((dimethylamino)methyl)-5-(trifluoromethyl)benzyl)-2,3-dihydro-1H-inden-2-yl)propane-2-sulfonamide a) (S)-N-(5-(3-(chloromethyl)-5-(trifluoromethyl)benzyl)-2,3-dihydro-1H-inden-2-yl)propane-2-sulfonamide

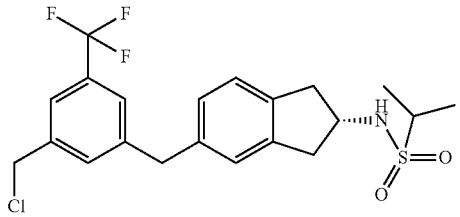 [SMILES: CC(C)S(=O)(=O)N[C@H]1Cc2ccc(Cc3cc(CCl)cc(C(F)(F)F)c3)cc2C1]

To a solution of (S)-N-(5-(3-(hydroxymethyl)-5-(trifluoromethyl)benzyl)-2,3-dihydro-1H-inden-2-yl)propane-2-sulfonamide (1.053 mmol, 450 mg) in CH2Cl2 (8 mL) was added Thionyl chloride (2.316 mmol, 0.169 mL, 276 mg) and the whole was stirred for 2 h at RT before the reaction mixture was concentrated under reduced pressure and re-dissovled in DCM. The process was repeated ×4 to drive off the excess thionyl chloride. The material was used immediately in the next reaction.

b) (S)-N-(5-(3-((dimethylamino)methyl)-5-(trifluoromethyl)benzyl)-2,3-dihydro-1H-inden-2-yl)propane-2-sulfonamide

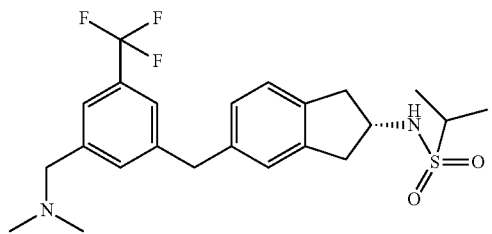 [SMILES: CC(C)S(=O)(=O)N[C@H]1Cc2ccc(Cc3cc(CN(C)C)cc(C(F)(F)F)c3)cc2C1]

To a solution of (S)-N-(5-(3-(chloromethyl)-5-(trifluoromethyl)benzyl)-2,3-dihydro-1H-inden-2-yl)propane-2-sulfonamide (0.090 mmol, 40 mg) in DMF (1 mL) was added dimethylamine (2M solution, 0.224 mmol, 0.112 mL). The whole was heated to 60° C. for 2 h before the reaction mixture was purified directly by prep HPLC to give the title compound. (21.2 mg, 52%). MS (ESI): m/z [M+H]+ 455.2

EXAMPLE 4

(S)-N-(5-(3-(azetidin-1-ylmethyl)-5-(trifluoromethyl)benzyl)-2,3-dihydro-1H-inden-2-yl)propane-2-sulfonamide

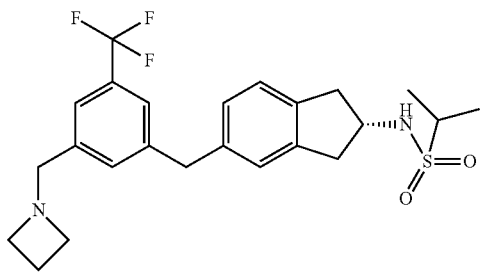 [SMILES: CC(C)S(=O)(=O)N[C@H]1Cc2ccc(Cc3cc(CN4CCC4)cc(C(F)(F)F)c3)cc2C1]

The title compound was prepared using a procedure analogous to Example 3b) using azetidine in place of dimethylamine. (17.9 mg, 42.8%). MS (ESI): m/z [M+H]+ 467.2

EXAMPLE 5

(S)-N-(5-(3-(pyrrolidin-1-ylmethyl)-5-(trifluoromethyl)benzyl)-2,3-dihydro-1H-inden-2-yl)propane-2-sulfonamide

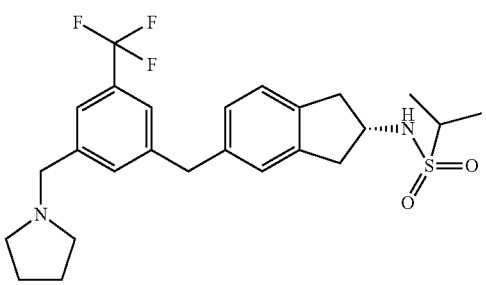 [SMILES: CC(C)S(=O)(=O)N[C@H]1Cc2ccc(Cc3cc(CN4CCCC4)cc(C(F)(F)F)c3)cc2C1]

The title compound was prepared using a procedure analogous to Example 3b) using pyrrolidine in place of dimethylamine. (21.1 mg, 48.9%). MS (ESI): m/z [M+H]+ 481.2

EXAMPLE 6

(S)-N-(5-(3-((2-hydroxyethylamino)methyl)-5-(trifluoromethyl)benzyl)-2,3-dihydro-1H-inden-2-yl)propane-2-sulfonamide

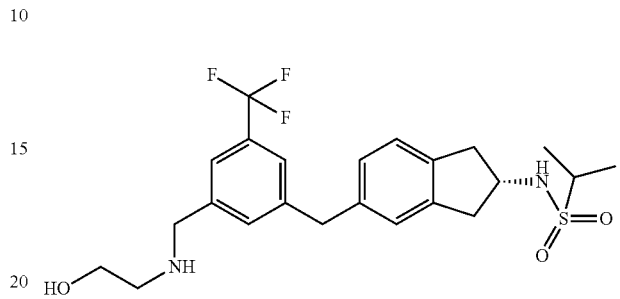

The title compound was prepared using a procedure analogous to Example 3b) using ethanolamine in place of dimethylamine. (12.1 mg, 28.7%). MS (ESI): m/z [M+H]+ 471.2

EXAMPLE 7

(S)-N-(5-(34 (1H-imidazol-1-yl)methyl)-5-(trifluoromethyl)benzyl)-2,3-dihydro-1H-inden-2-yl)propane-2-sulfonamide

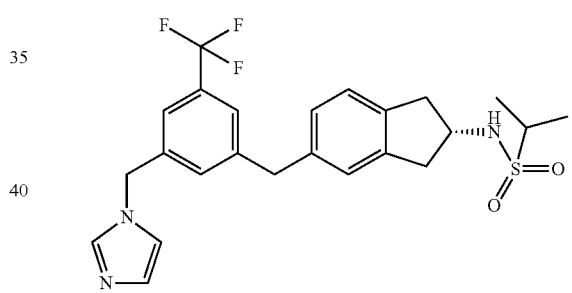

The title compound was prepared using a procedure analogous to Example 3b) using imidazole in place of dimethylamine. (10.6 mg, 24.8%). MS (ESI): m/z [M+H]+ 478.2

EXAMPLE 8

(S)-N-(5-(3-((methylamino)methyl)-5-(trifluoromethyl)benzyl)-2,3-dihydro-1H-inden-2-yl)propane-2-sulfonamide

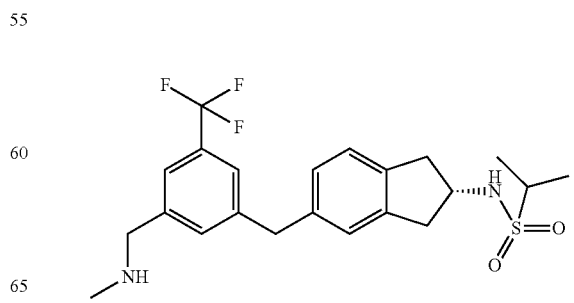

The title compound was prepared using a procedure analogous to Example 3b) using methylamine (2M solution) in place of dimethylamine. (5.8 mg, 11.7%). MS (ESI): m/z [M+H]+ 478.2

EXAMPLE 9

(S)-N-(5-(3-(trifluoromethyl)phenoxy)-2,3-dihydro-1H-inden-2-yl)propane-2-sulfonamide a) (S)-N-(5-(4,4,5,5-tetramethyl-1,3,2-dioxaborolan-2-yl)-2,3-dihydro-1H-inden-2-yl)propane-2-sulfonamide

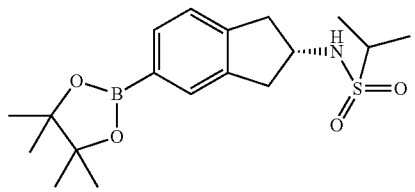 [SMILES: CC(C)S(=O)(=O)N[C@H]1Cc2ccc(B3OC(C)(C)C(C)(C)O3)cc2C1]

A solution of (S)-N-(5-bromo-2,3-dihydro-1H-inden-2-yl)propane-2-sulfonamide (9.02 mmol, 2.87 g), 4,4,4',4',5,5,5',5'-octamethyl-2,2'-bi(1,3,2-dioxaborolane) (22.55 mmol, 5.73 g), potassium acetate (36.1 mmol, 3.54 g) and 1,1'-bis(diphenylphosphino)ferrocenedichloropalladium(II) (0.271 mmol, 0.196 g) in DMF (40 mL) was heated at 60° C. for 2 days under nitrogen. The reaction mixture was concentrated before partitioning between EtOAc/Water and filtration through a dicalite plug. The phases were mixed and separated and the organic layer washed with water then brine. Concentration followed by purification on silica (eluting with 15% EtOAc/Heptane) the desired compound as a white solid (2.54 g, 77%). $^1$H NMR (400 MHz, CDCl$_3$) δ 1.3 (s, 12H) 1.39 (d, 6H) 2.89 (m, 2H) 3.18 (sept, 1H) 3.30 (m, 2H) 4.28 (m, 1H) 4.41 (m, 1H), 7.18 (m, 2H) 7.64 (m, 1H).

b) (S)-N-(5-hydroxy-2,3-dihydro-1H-inden-2-yl)propane-2-sulfonamide

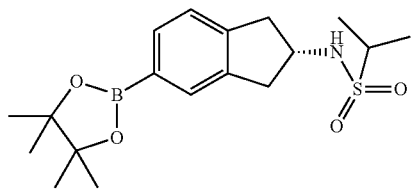 [SMILES: CC(C)S(=O)(=O)N[C@H]1Cc2ccc(B3OC(C)(C)C(C)(C)O3)cc2C1]

To a stirred solution of (S)-N-(5-(4,4,5,5-tetramethyl-1,3,2-dioxaborolan-2-yl)-2,3-dihydro-1H-inden-2-yl)propane-2-sulfonamide (6.95 mmol, 2.54 g) in Acetone (20.00 mL), a solution of Oxone(R), monopersulfate compound (7.65 mmol, 4.70 g) in Water (20 mL) was added dropwise over 2 min. The resultant solution was stirred for a further 10 min before being quenched with NaHSO$_3$ (aq). The solution was extracted with DCM (×3), dried (MgSO$_4$), filtered and concentrated in vacuo to give the crude product as a pale yellow oil (2.42 g). On standing the reaction mixture solidified to a pale yellow solid in an oily residue. The solid was triturated with heptane then ether to give the title compound as an off white solid (1.66 g, 94%). MS (ESI): m/z [M−H]− 254.0 c) (S)-N-(5-(3-(trifluoromethyl)phenoxy)-2,3-dihydro-1H-inden-2-yl)propane-2-sulfonamide

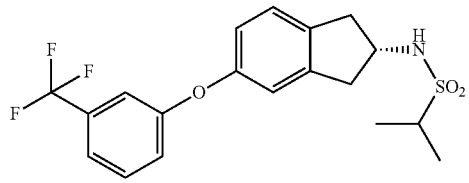 [SMILES: CC(C)S(=O)(=O)N[C@H]1Cc2ccc(Oc3cccc(C(F)(F)F)c3)cc2C1]

To a mixture of the 3-trifluoromethyphenyl boronic acid (0.274 mmol, 52 mg), copper (II) acetate (0.137 mmol, 25 mg), triethylamine (0.685 mmol, 96 µL) and 4A molecular sieves (100 mg) in DCM (1 mL) was added (S)-N-(5-hydroxy-2,3-dihydro-1H-inden-2-yl)propane-2-sulfonamide (0.137 mmol, 35 mg) and the resultant mixture stirred at room temperature overnight. The reaction mixture was diluted with DCM (1 mL) before water (0.5 mL) was added and the organic layers separated using hydrophobic frits. The aqueous was extracted with a further 1 mL DCM, and the combined organics concentrated using to dryness. The residue was taken up in DMSO and purified by preparative HPLC to give the title compound as a clear film (21.9 mg, 40%). MS (ESI): m/z [M+H]+ 400.0

EXAMPLE 10

(S)-N-methyl-3-(2-(1-methylethylsulfonamido)-2,3-dihydro-1H-inden-5-yloxy)benzene sulphonamide

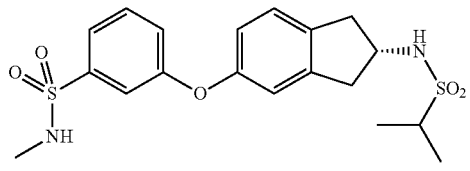 [SMILES: CNS(=O)(=O)c1cccc(Oc2ccc3c(c2)C[C@@H](NS(=O)(=O)C(C)C)C3)c1]

The title compound was prepared using the procedure detailed in Example 9c using 3-(N-methylsulfamoyl)phenylboronic acid instead of 3-trifluoromethylphenyl boronic acid. (11.5 mg, 19.8%). MS (ESI): m/z [M−H]− 423.0

EXAMPLE 11

(S)-N-(5-(6-(trifluoromethyl)pyridin-2-yloxy)-2,3-dihydro-1H-inden-2-yl)propane-2-sulfonamide

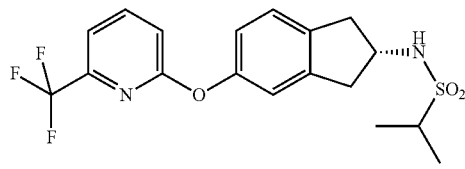 [SMILES: CC(C)S(=O)(=O)N[C@H]1Cc2ccc(Oc3cccc(C(F)(F)F)n3)cc2C1]

The title compound was prepared using the procedure detailed in Example 9c using 2-(4,4,5,5-tetramethyl-1,3,2- dioxaborolan-2-yl)-6-(trifluoromethyl)pyridine instead of 3-trifluoromethylphenyl boronic acid (5.9 mg, 10.8%). MS (ESI): m/z [M–H]⁻ 399.0

EXAMPLE 12

(S)-N-(5-(2-(trifluoromethyl)pyridin-4-yloxy)-2,3-dihydro-1H-inden-2-yl)propane-2-sulfonamide

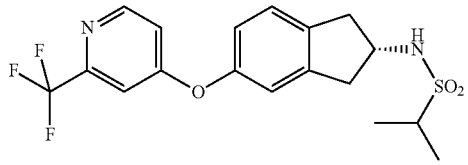 [SMILES: CC(C)S(=O)(=O)N[C@H]1Cc2ccc(Oc3ccnc(C(F)(F)F)c3)cc2C1]

The title compound was prepared using the procedure detailed in Example 9c using 4-(4,4,5,5-tetramethyl-1,3,2-dioxaborolan-2-yl)-2-(trifluoromethyl)pyridine instead of 3-trifluoromethylphenyl boronic acid (11.3 mg, 20.6%). MS (ESI): m/z [M–H]⁻ 399.0

EXAMPLE 13

(S)-N-(5-(3-(methylsulfonamidomethyl)phenoxy)-2,3-dihydro-1H-inden-2-yl)propane-2-sulfonamide

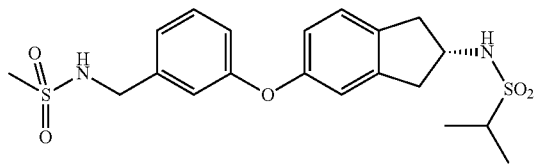 [SMILES: CC(C)S(=O)(=O)N[C@H]1Cc2ccc(Oc3cccc(CNS(C)(=O)=O)c3)cc2C1]

The title compound was prepared using the procedure detailed in Example 9c using 3-(methylsulfonamidomethyl)phenylboronic acid instead of 3-trifluoromethylphenyl boronic acid (4.2 mg, 7.0%). MS (ESI): m/z [M–H]⁻ 437.0

EXAMPLE 14

(S)-N-(5-(4-cyanophenoxy)-2,3-dihydro-1H-inden-2-yl)propane-2-sulfonamide

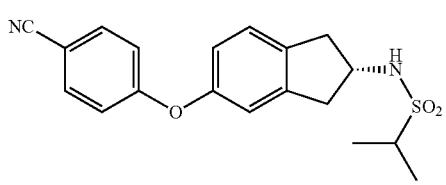 [SMILES: CC(C)S(=O)(=O)N[C@H]1Cc2ccc(Oc3ccc(C#N)cc3)cc2C1]

The title compound was prepared using the procedure detailed in Example 9c using 4-cyanophenylboronic acid instead of 3-trifluoromethylphenyl boronic acid (6.1 mg, 12.5%). MS (ESI): m/z [M–H]⁻ 355.0

EXAMPLE 15

(S)-N-methyl-3-(2-(1-methylethylsulfonamido)-2,3-dihydro-1H-inden-5-yloxy)benzamide

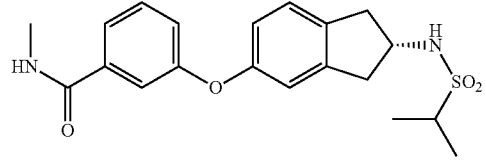 [SMILES: CNC(=O)c1cccc(Oc2ccc3c(c2)C[C@@H](NS(=O)(=O)C(C)C)C3)c1]

The title compound was prepared using the procedure detailed in Example 9c using 3-(methylcarbamoyl)phenylboronic acid instead of 3-trifluoromethylphenyl boronic acid (5.3 mg, 10.0%). MS (ESI): m/z [M–H]⁻ 387.0

EXAMPLE 16

(S)-3-(2-(1-methylethylsulfonamido)-2,3-dihydro-1H-inden-5-yloxy)benzenesulfonamide

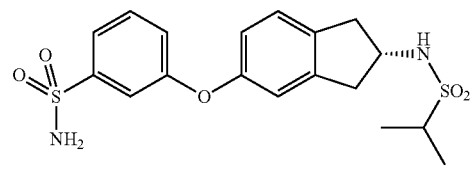 [SMILES: CC(C)S(=O)(=O)N[C@H]1Cc2ccc(Oc3cccc(S(N)(=O)=O)c3)cc2C1]

The title compound was prepared using the procedure detailed in Example 9c using 3-sulfamoylphenylboronic acid instead of 3-trifluoromethylphenyl boronic acid (3.1 mg, 5.5%). MS (ESI): m/z [M–H]⁻ 409.0

EXAMPLE 17

(S)-N-(5-(3-(methylsulfonyl)phenoxy)-2,3-dihydro-1H-inden-2-yl)propane-2-sulfonamide

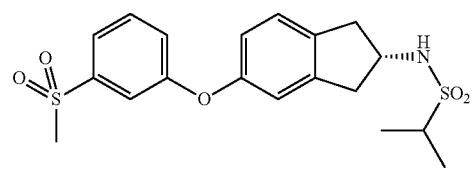 [SMILES: CC(C)S(=O)(=O)N[C@H]1Cc2ccc(Oc3cccc(S(C)(=O)=O)c3)cc2C1]

The title compound was prepared using the procedure detailed in Example 9c using 3-(methylsulfonyl)phenylboronic acid instead of 3-trifluoromethylphenyl boronic acid (2.0 mg, 3.6%). MS (ESI): m/z [M–H]⁻ 408.0

EXAMPLE 18

(S)-N-(5-(3-(methylsulfonamido)phenoxy)-2,3-dihydro-1H-inden-2-yl)propane-2-sulfonamide

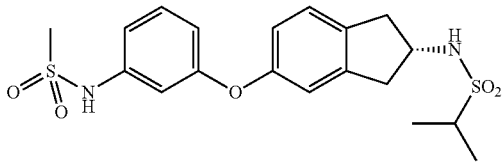 [SMILES: CC(C)S(=O)(=O)N[C@H]1Cc2ccc(Oc3cccc(NS(C)(=O)=O)c3)cc2C1]

The title compound was prepared using the procedure detailed in Example 9c using 3-(methylsulfonyl)phenylboronic acid instead of 3-trifluoromethylphenyl boronic acid (1.3 mg, 2.2%). MS (ESI): m/z [M−H]⁻ 423.0

EXAMPLE 19

(S)-N-(5-(benzo[c][1,2,5]oxadiazol-4-yloxy)-2,3-dihydro-1H-inden-2-yl)propane-2-sulfonamide

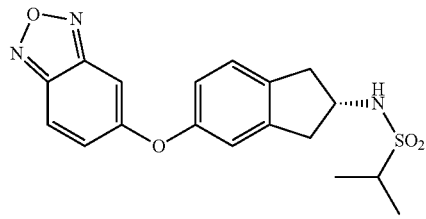 [SMILES: CC(C)S(=O)(=O)N[C@H]1Cc2ccc(Oc3ccc4nonc4c3)cc2C1]

The title compound was prepared using the procedure detailed in Example 9c using benzo[c][1,2,5]oxadiazol-4-ylboronic acid instead of 3-trifluoromethylphenyl boronic acid (1.3 mg, 2.2%). MS (ESI): m/z [M−H]⁻ 372.0

EXAMPLE 20

N-(5-(2-fluorobenzyl)-2,3-dihydro-1H-inden-1-yl)propane-2-sulfonamide a) (E)-5-bromo-2,3-dihydro-1H-inden-1-one Oxime

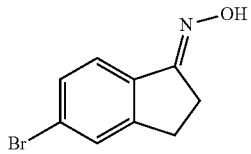

5-bromo-2,3-dihydro-1H-inden-1-one (25 g, 118 mmol) and hydroxylamine hydrochloride (12.35 g, 178 mmol) were heated in Ethanol (150 mL) for 5 hours with stirring. The solvent was evaporated in vacuo and remaining solid partitioned between H₂O and EtOAc. The organic layer was separated and washed with brine (2×), dried on Na₂SO₄ and solvent evaporated in vacuo to afford the title compound as a light brown solid (23.6 g, 87%). MS (ESI): m/z [M+H]⁺ 227.0 b) 5-bromo-2,3-dihydro-1H-inden-1-amine

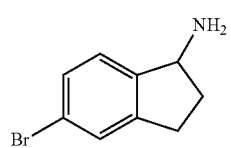 [SMILES: NC1CCc2cc(Br)ccc21]

Zinc dust (28.0 g, 428 mmol) was added to a suspension of (E)-5-bromo-2,3-dihydro-1H-inden-1-one oxime (19.4 g, 86 mmol) in acetic acid (30 mL). The suspension was stirred at rt for 48 h. The reaction was filtered over Kiezelguhr gel. The residue was rinsed with ethyl acetate (2×100 mL). The combined filtrates were concentrated under reduced pressure to obtain a yellow oil. The yellow oil was partitioned between ethyl acetate (200 mL) and 2 N aq. HCl (200 mL). The acidic layer was separated before being basified using aq. 4 N NaOH and a white suspension was formed. Ethyl acetate (200 mL) was added and the milky mixture was filtered over Kiezelguhr gel. The organic phase was separated, dried over sodium sulfate, filtered, and concentrated under reduced pressure to afford the title compound as a clear light yellow oil (10.8 g, 59%). MS (ESI): m/z [M−NH₂]⁺ 198.0 c) N-(5-bromo-2,3-dihydro-1H-inden-1-yl)propane-2-sulfonamide

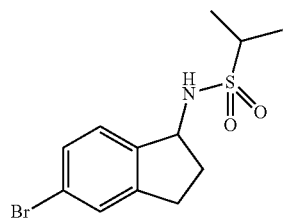 [SMILES: CC(C)S(=O)(=O)NC1CCc2cc(Br)ccc21]

At 0° C. and under protective atmosphere, a solution of 2-Propanesulfonyl chloride (11.87 mL, 121 mmol) in DCM (121 mL) was added gradually to a solution of 5-bromo-2,3-dihydro-1H-inden-1-amine (12.8 g, 60.4 mmol) and 1,8-Diazabicyclo[5.4.0]undec-7-ene (4.83 mL, 32.1 mmol) in Dichloromethane (300 mL). The reaction was stirred at rt overnight. The reaction mixture was washed with 1N KHSO₄ (1×) and sat NaHCO₃ (2×) before being dried on Na₂SO₄ and solvent evaporated in vacuo to afford a green oil. Purification by column chromatography (25% EtOAc in heptane) afforded the title compound as a white solid.

(6.0 g, 31%). MS (ESI): m/z [M−H]⁻ 317.0 d) N-(5-(4,4,5,5-tetramethyl-1,3,2-dioxaborolan-2-yl)-2,3-dihydro-1H-inden-1-yl)propane-2-sulfonamide

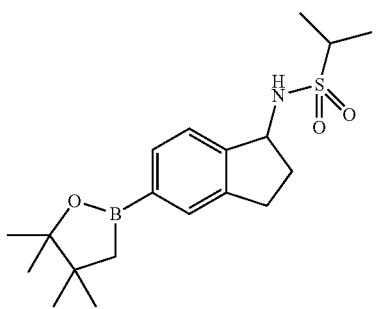 [SMILES: CC(C)S(=O)(=O)NC1CCc2cc(B3CC(C)(C)C(C)(C)O3)ccc21]

A mixture of N-(5-bromo-2,3-dihydro-1H-inden-1-yl)propane-2-sulfonamide (2.20 g, 6.9 mmol), potassium acetate (2.01 g, 20.5 mmol), bis(pinacolato)diboron (2.10 g, 8.3 mmol), and 1,1-BIS(diphenylphosphino)ferrocenepalladium(II)dichloride (240 mg, 0.29 mmol) in DMSO (40 mL) was stirred at 90° C. for 3 h. The reaction was cooled to rt and filtered over Kiezelguhr gel. The filter cake was rinsed with EtOAc before the filtrate was diluted with EtOAc (200 mL) and washed with brine (3×200 mL). The organic phase was dried over sodium sulfate, filtered, and concentrated under reduced pressure to afford a brown/yellow oil. The residue was purified by flash column chromatography (EtOAc/heptane, from 0% to 50% of heptane) to afford the title compound as a white foam. (2.49 g, 99%). MS (ESI): m/z $[M+NH_4]^+$ 317.0 e) N-(5-(2-fluorobenzyl)-2,3-dihydro-1H-inden-1-yl)propane-2-sulfonamide

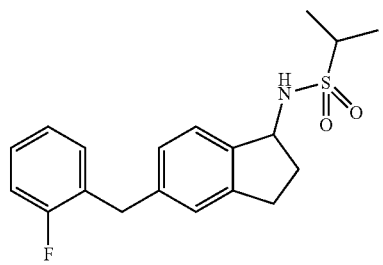 [SMILES: CC(C)S(=O)(=O)NC1CCc2cc(Cc3ccccc3F)ccc21]

A mixture of 2-fluorobenzyl bromide (33 µL, 0.27 mmol), N-(5-(4,4,5,5-tetramethyl-1,3,2-dioxaborolan-2-yl)-2,3-dihydro-1H-inden-1-yl)propane-2-sulfonamide (100 mg, 0.27 mmol), trans-Bromo(N-succinimidyl)bis(triphenylphosphine)palladium(II) (11 mg, 0.014 mmol), and sodium carbonate (145 mg, 1.37 mmol) in degassed tetrahydrofuran (1.33 mL) and water (0.66 mL) was stirred at 80° C. for 16 h. The reaction was then diluted with 6 mL of DCM and 2 mL of water and the mixture was filtered over a phase separator. The organic phase was evaporated to dryness in vacuo to afford a brown oil in. Purification by silica flash column chromatography (EtOAc/heptane: from 0% to 60% of EtOAc) afforded the title compound as an oil (63.1 mg, 66%). MS (ESI): m/z $[M-H]^-$ 346.0

EXAMPLE 21

N-(5-(3-methoxybenzyl)-2,3-dihydro-1H-inden-1-yl)propane-2-sulfonamide

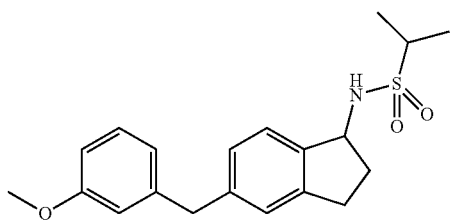 [SMILES: COc1cccc(Cc2ccc3c(c2)CCC3NS(=O)(=O)C(C)C)c1]

The title compound was prepared using the procedure detailed in Example 20e using 3-Methoxybenzyl chloride instead of 2-fluorobenzyl bromide (50.2 mg, 51%). MS (ESI): m/z $[M-H]^-$ 472.0

EXAMPLE 22

N-(5-(3-(trifluoromethyl)benzyl)-2,3-dihydro-1H-inden-1-yl)propane-2-sulfonamide

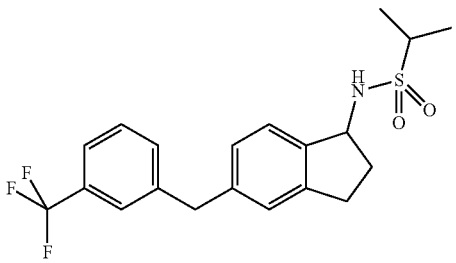 [SMILES: CC(C)S(=O)(=O)NC1CCc2cc(Cc3cccc(C(F)(F)F)c3)ccc21]

The title compound was prepared using the procedure detailed in Example 20e using 3-trifluoromethylbenzyl chloride instead of 2-fluorobenzyl bromide (5.0 mg, 4.6%). MS (ESI): m/z $[M-H]^-$ 396.0

EXAMPLE 23

N-(5-(3-methylbenzyl)-2,3-dihydro-1H-inden-1-yl)propane-2-sulfonamide

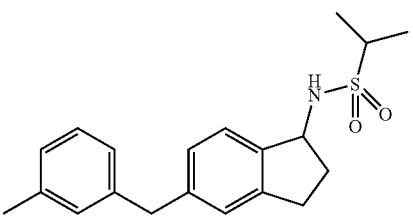 [SMILES: Cc1cccc(Cc2ccc3c(c2)CCC3NS(=O)(=O)C(C)C)c1]

The title compound was prepared using the procedure detailed in Example 20e using 3-methylbenzyl bromide instead of 2-fluorobenzyl bromide (41 mg, 44%). MS (ESI): m/z [M−H]⁻ 342.2

EXAMPLE 24

N-(5-(3-cyanobenzyl)-2,3-dihydro-1H-inden-1-yl)propane-2-sulfonamide

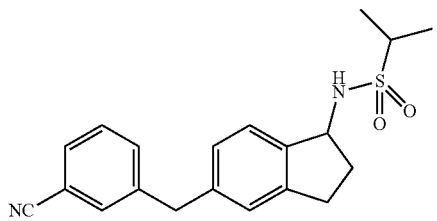 [SMILES: CC(C)S(=O)(=O)NC1CCc2cc(Cc3cccc(C#N)c3)ccc21]

The title compound was prepared using the procedure detailed in Example 20e using alpha-Bromo-m-tolunitrile instead of 2-fluorobenzyl bromide (65.7 mg, 67.7%). MS (ESI): m/z [M−H]⁻ 342.2

EXAMPLE 25

N-(5-(3-chlorobenzyl)-2,3-dihydro-1H-inden-1-yl)propane-2-sulfonamide a) methyl 1-(1-methylethylsulfonamido)-2,3-dihydro-1H-indene-5-carboxylate

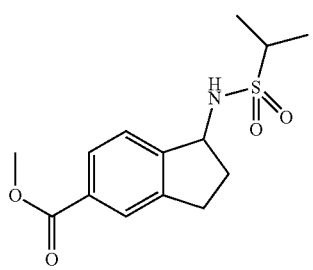 [SMILES: COC(=O)c1ccc2c(c1)CCC2NS(=O)(=O)C(C)C]

A 150 mL steel autoclave was charged with N-(5-bromo-2,3-dihydro-1H-inden-1-yl)propane-2-sulfonamide (4.85 g, 15.24 mmol), 1,1'-bis(Diphenylphosphino) ferrocenepalladium(II)dichloride (0.622 g, 0.762 mmol), and sodium carbonate (3.23 g, 30.5 mmol) in degassed and methanol. The autoclave was placed under carbon monoxide atmosphere (12 bar) and stirred at 100° C. for 24 hr. After this time, catalyst and Na₂CO₃ were filtered off and replaced with a new batch and the reaction was stirred for 24 hr at 100° C. and 12 bar CO. The mixture was filtered and partitioned between EtOAc and brine, organic layer separated, washed with brine. To the organic layer was added silica and Na₂SO₄ added and stirred for 20 min. The whole was filtered and solvent evaporated in vacuo to give a brown oil. Purification by flash chromatography (0-50% EtOAc in heptane) afforded the title compound as a yellow/brown oil (1 g, 22%).

b) N-(5-(hydroxymethyl)-2,3-dihydro-1H-inden-1-yl)propane-2-sulfonamide

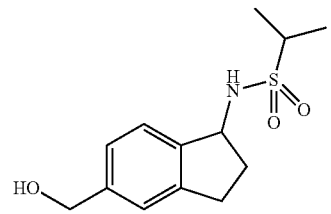 [SMILES: CC(C)S(=O)(=O)NC1CCc2cc(CO)ccc21]

At 0° C. Lithium Aluminium Hydride (2.102 mL, 5.04 mmol) was added dropwise to a stirred solution of methyl 1-(1-methylethylsulfonamido)-2,3-dihydro-1H-indene-5-carboxylate (1 g, 3.36 mmol) in Tetrahydrofuran (dry) (25 mL). Mixture warmed to rt and stirred for 4 hr. After this time the reaction mixture was again cooled to 0° C. and more Lithium Aluminium Hydride (2.102 mL, 5.04 mmol) added and the whole stirred at room temperature for 30 min before being carefully quenched with H₂O (10 mL) and 2N NaOH (10 mL). The resulting mixture was filtered and partitioned between EtOAc and brine. The organic layer was separated, dried on Na₂SO₄ and solvent evaporated in vacuo to give a dark yellow oil Purification by flash chromatography (0-100% EtOAc in Heptane) afforded the title compound as a colourless oil (670 mg, 74%). MS (ESI): m/z [M−H]⁻ 268.0 c) N-(5-(chloromethyl)-2,3-dihydro-1H-inden-1-yl)propane-2-sulfonamide

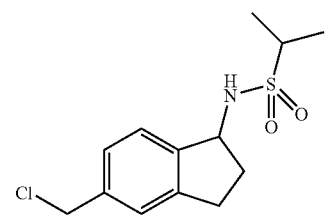 [SMILES: CC(C)S(=O)(=O)NC1CCc2cc(CCl)ccc21]

Thionyl chloride (0.355 mL, 4.90 mmol) was added to a solution of N-(5-(hydroxymethyl)-2,3-dihydro-1H-inden-1-yl)propane-2-sulfonamide (660 mg, 2.450 mmol) in DCM (10 mL). The whole was stirred for 1 h before the reaction mixture was evaporated to dryness and the crude material was purified by silica flash column chromatography (EtOAc/heptane: from 0% to 60% of EtOAc) to afford the title compound as a white solid (360 mg, 51%). MS (ESI): m/z [M−H]⁻ 286.0 d) N-(5-(3-chlorobenzyl)-2,3-dihydro-1H-inden-1-yl)propane-2-sulfonamide

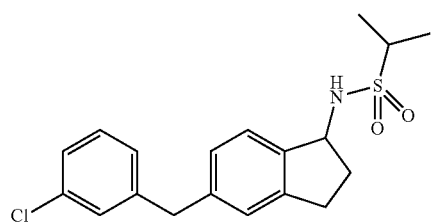 [SMILES: CC(C)S(=O)(=O)NC1CCc2cc(Cc3cccc(Cl)c3)ccc21]

A mixture of N-(5-(chloromethyl)-2,3-dihydro-1H-inden-1-yl)propane-2-sulfonamide (50 mg, 0.174 mmol), 3-chlorophenylboronic acid (54.3 mg, 0.347 mmol), trans-Bromo(N-succinimidyl)bis(triphenylphosphine)palladium(II) (7.04 mg, 8.69 μmol), and Sodium carbonate (36.8 mg, 0.347 mmol) in degassed Tetrahydrofuran (1 mL) and Water (1 mL) was stirred at 60° C. for 5 h. The Reaction mixture was then filtered and partitioned between H$_2$O and EtOAc, the organic layer separated and evaporated in vacuo. Purification by flash chromatography (0-100% EtOAc in heptane) afforded the title compound as a colourless oil (43 mg, 68%). MS (ESI): m/z [M−H]⁻ 362.0

EXAMPLE 26

N-(5-(3-(methylsulfonyl)benzyl)-2,3-dihydro-1H-inden-1-yl)propane-2-sulfonamide

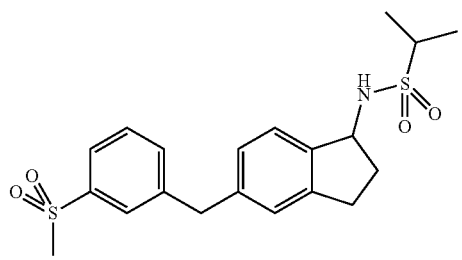 [SMILES: CC(C)S(=O)(=O)NC1CCc2cc(Cc3cccc(S(C)(=O)=O)c3)ccc21]

The title compound was prepared using the procedure detailed in Example 25d using 3-(methylsulfonyl)phenylboronic acid instead of 3-chlorophenylboronic acid (41 mg, 57.9%). MS (ESI): m/z [M−H]⁻ 406.0

EXAMPLE 27

N-methyl-3-((1-(1-methylethylsulfonamido)-2,3-dihydro-1H-inden-5-yl)methyl)benzene sulphonamide

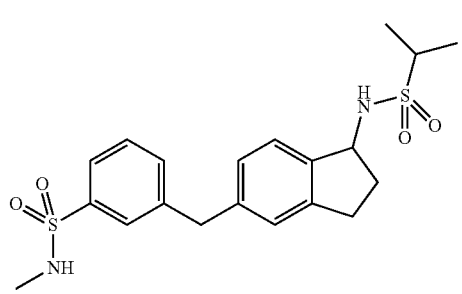 [SMILES: CNS(=O)(=O)c1cccc(Cc2ccc3c(c2)CCC3NS(=O)(=O)C(C)C)c1]

The title compound was prepared using the procedure detailed in Example 25d using 3-(N-methylsulfamoyl)phenylboronic acid instead of 3-chlorophenylboronic acid (45 mg, 61.3%). MS (ESI): m/z [M+NH$_4$]⁺ 440.0

EXAMPLE 28

N-(5-(3-(methylsulfonamido)benzyl)-2,3-dihydro-1H-inden-1-yl)propane-2-sulfonamide

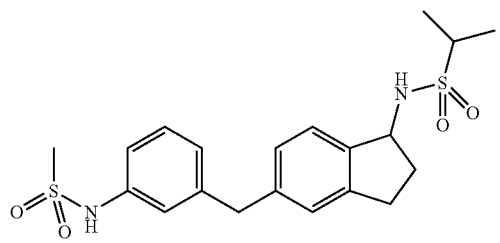 [SMILES: CC(C)S(=O)(=O)NC1CCc2cc(Cc3cccc(NS(C)(=O)=O)c3)ccc21]

The title compound was prepared using the procedure detailed in Example 25d using 3-(methylsulfonamido)phenylboronic acid instead of 3-chlorophenylboronic acid (35 mg, 47.6%). MS (ESI): m/z [M−H]⁻ 421.0

EXAMPLE 29

N-(5-(5-methoxypyridin-3-yloxy)-2,3-dihydro-1H-inden-1-yl)propane-2-sulfonamide a) N-(5-hydroxy-2,3-dihydro-1H-inden-1-yl)propane-2-sulfonamide

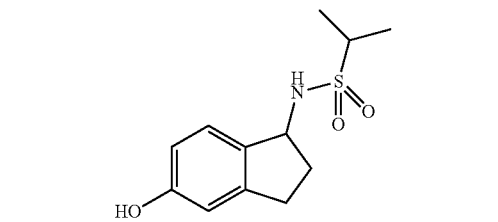 [SMILES: CC(C)S(=O)(=O)NC1CCc2cc(O)ccc21]

To a stirred solution of N-(5-(4,4,5,5-tetramethyl-1,3,2-dioxaborolan-2-yl)-2,3-dihydro-1H-inden-1-yl)propane-2-sulfonamide (1.5 g, 4.11 mmol) in acetone (15 mL) was added dropwise a solution of oxone (2.78 g, 4.52 mmol) in water (15 mL). The resulting mixture stirred for another 10 min before the reaction mixture quenched with Na$_2$O$_5$S$_2$ solution and diluted with DCM. The organic layer was separated, washed with brine (2×) and dried on Na$_2$SO$_4$. Solvent evaporated in vacuo to afford the title compound as a white solid (1.05 g, 100%). MS (ESI): m/z [M−H]⁻ 254.0 b) N-(5-(5-methoxypyridin-3-yloxy)-2,3-dihydro-1H-inden-1-yl)propane-2-sulfonamide

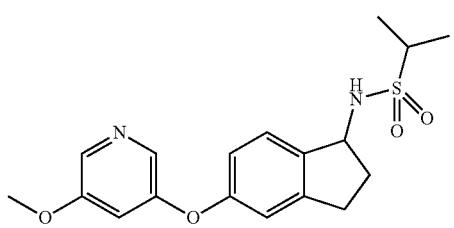 [SMILES: COc1cncc(Oc2ccc3c(c2)CCC3NS(=O)(=O)C(C)C)c1]

A mixture of N-(5-hydroxy-2,3-dihydro-1H-inden-1-yl)propane-2-sulfonamide (50.0 mg, 0.196 mmol), 5-methoxypyridin-3-ylboronic acid (90 mg, 0.587 mmol), Copper(II) acetate (35.6 mg, 0.196 mmol), triethylamine (0.136 mL, 0.979 mmol), and crushed 4 Å molecular sieves (150 mg) in Dichloromethane (2 mL) was stirred at rt for 3 days. After this time the reaction mixture was filtered and solvent evaporated in vacuo. Purification by flash chromatography (heptane:EtOAc 3:1) afforded the title compound as a white solid. (6.7 mg, 9.4%). MS (ESI): m/z [M−H]⁻ 361.0

EXAMPLE 30

N-Methyl-3-(1-(1-methylethylsulfonamido)-2,3-dihydro-1H-inden-5-yloxy)benzene sulphonamide

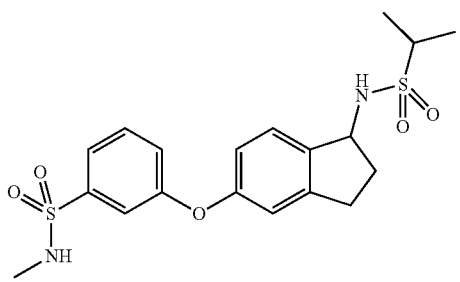 [SMILES: CNS(=O)(=O)c1cccc(Oc2ccc3c(c2)CCC3NS(=O)(=O)C(C)C)c1]

The title compound was prepared using the procedure detailed in Example 29b using 3-(N-methylsulfamoyl)phenylboronic acid instead of 5-methoxypyridin-3-ylboronic acid (1.8 mg, 1.9%). MS (ESI): m/z [M−H]⁻ 423.0

EXAMPLE 31

N-(5-(3-(methylsulfonamidomethyl)phenoxy)-2,3-dihydro-1H-inden-1-yl)propane-2-sulfonamide

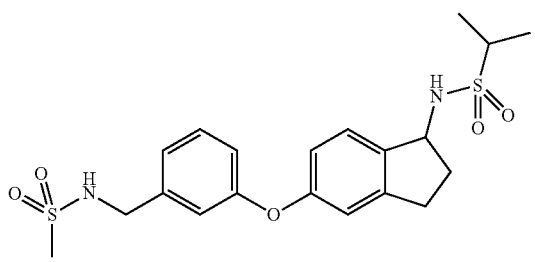 [SMILES: CC(C)S(=O)(=O)NC1CCc2cc(Oc3cccc(CNS(C)(=O)=O)c3)ccc21]

The title compound was prepared using the procedure detailed in Example 29b using 3-(methylsulfonamidomethyl)phenylboronic acid instead of 5-methoxypyridin-3-ylboronic acid (3.7 mg, 4.3%). MS (ESI): m/z [M−H]⁻ 437.0

EXAMPLE 32

N-(5-(3-(methylsulfonamido)phenoxy)-2,3-dihydro-1H-inden-1-yl)propane-2-sulfonamide

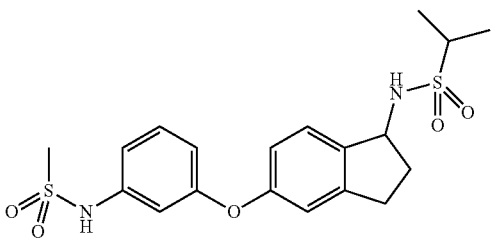 [SMILES: CC(C)S(=O)(=O)NC1CCc2cc(Oc3cccc(NS(C)(=O)=O)c3)ccc21]

The title compound was prepared using the procedure detailed in Example 29b using 3-(methylsulfonamido)phenylboronic acid instead of 5-methoxypyridin-3-ylboronic acid (9.4 mg, 1.3%). MS (ESI): m/z [M−H]⁻ 423.0

EXAMPLE 33

N-(5-(benzo[c][1,2,5]oxadiazol-5-yloxy)-2,3-dihydro-1H-inden-1-yl)propane-2-sulfonamide

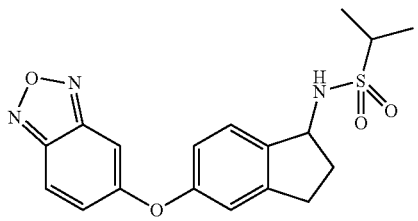 [SMILES: CC(C)S(=O)(=O)NC1CCc2cc(Oc3ccc4nonc4c3)ccc21]

A mixture of 5-(4,4,5,5-tetramethyl-1,3,2-dioxaborolan-2-yl)benzo[c][1,2,5]oxadiazole (0.313 mmol, 77 mg), N-(5-hydroxy-2,3-dihydro-1H-inden-1-yl)propane-2-sulfonamide (0.157 mmol, 40 mg), copper (II)acetate (0.157 mmol, 28.5 mg), triethylamine (0.783 mmol, 0.110 mL, 79 mg) and 4A molecular sieves (100 mg) in DCM (1 mL) was stirred at room temperature for 60 h. The reaction mixture was filtered through dicalite and the pad washed with MeOH before the filtrate was concentrated to dryness. The residue was purified by prep HPLC to give a brown film (32. mg, 5.5%). MS (ESI): m/z [M+H]⁺ 374.0

EXAMPLE 34

N-(5-(2-(trifluoromethyl)pyridin-4-yloxy)-2,3-dihydro-1H-inden-1-yl)propane-2-sulfonamide

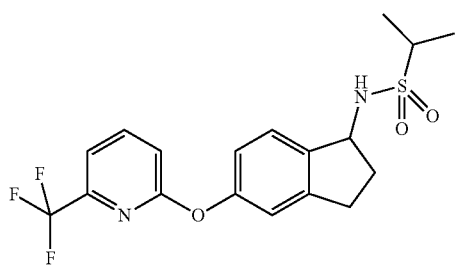 [SMILES: CC(C)S(=O)(=O)NC1CCc2cc(Oc3cccc(C(F)(F)F)n3)ccc21]

The title compound was prepared using the procedure detailed in Example 33 using 4-(4,4,5,5-tetramethyl-1,3,2-dioxaborolan-2-yl)-2-(trifluoromethyl)pyridine instead of 5-(4,4,5,5-tetramethyl-1,3,2-dioxaborolan-2-yl)benzo[c][1,2,5]oxadiazole (12.8 mg, 20.8%). MS (ESI): m/z [M+H]+ 401.0

EXAMPLE 35

N-(5-(2-(trifluoromethyl)benzyloxy)-2,3-dihydro-1H-inden-1-yl)propane-2-sulfonamide

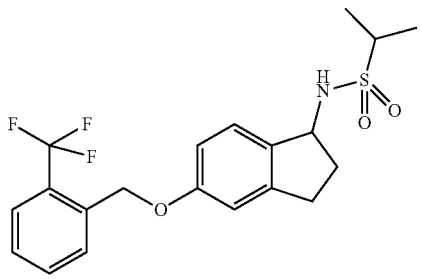 [SMILES: CC(C)S(=O)(=O)NC1CCc2cc(OCc3ccccc3C(F)(F)F)ccc21]

N-(5-hydroxy-2,3-dihydro-1H-inden-1-yl)propane-2-sulfonamide (50 mg, 0.196 mmol) was dissolved in N,N-dimethylformamide (dry) (2 mL), potassium carbonate (54.1 mg, 0.392 mmol) and 1-(bromomethyl)-2-(trifluoromethyl)benzene (94 mg, 0.392 mmol) were added and the mixture was stirred at 60° C. for 3 hr. After this time, the reaction mixture was partitioned between EtOAc and $H_2O$, the organic layer separated and solvent evaporated in vacuo. Purification by flash chromatography (0-100% EtOAc in heptane) afforded the title compound as a colourless oil (34 mg, 42%). MS (ESI): m/z [M−H]− 412.0

EXAMPLE 36

N-(5-(2-(difluoromethoxy)benzyloxy)-2,3-dihydro-1H-inden-1-yl)propane-2-sulfonamide

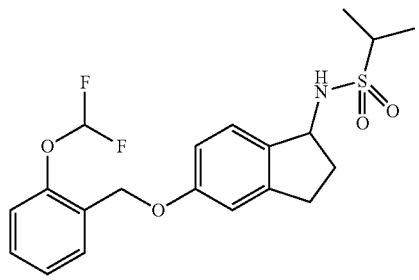 [SMILES: CC(C)S(=O)(=O)NC1CCc2cc(OCc3ccccc3OC(F)F)ccc21]

The title compound was prepared using the procedure detailed in Example 35 using 1-(bromomethyl)-2-(difluoromethoxy)benzene instead of 1-(bromomethyl)-2-(trifluoromethyl)benzene (36 mg, 44.7%). MS (ESI): m/z [M−H]− 410.0

EXAMPLE 37

N-(5-((2-(trifluoromethyl)phenoxy)methyl)-2,3-dihydro-1H-inden-1-yl)propane-2-sulfonamide

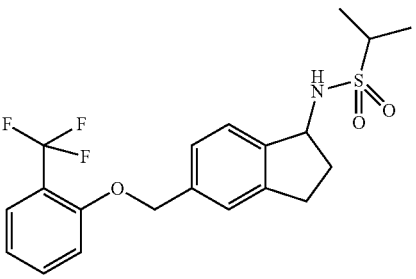 [SMILES: CC(C)S(=O)(=O)NC1CCc2cc(COc3ccccc3C(F)(F)F)ccc21]

A mixture of N-(5-(chloromethyl)-2,3-dihydro-1H-inden-1-yl)propane-2-sulfonamide (30 mg, 0.104 mmol), 2-(trifluoromethyl)phenol (16.90 mg, 0.104 mmol), and potassium carbonate (28.8 mg, 0.208 mmol) in N,N-dimethylformamide (1 mL) was stirred at 60° C. overnight. The reaction mixture was partitioned between aq. sat. $NaHCO_3$ (4 mL) and DCM (4 mL), filtered over a phase separator, and the organic phase was concentrated by blow down. Purification by flash chromatography (0-60% EtOAc in Heptane) and freeze drying from acetonitrile/water gave the title compound as a white solid (24 mg, 55.7%). MS (ESI): m/z [M−H]− 412.0.

EXAMPLE 38

N-(5-((2-chlorophenoxy)methyl)-2,3-dihydro-1H-inden-1-yl)propane-2-sulfonamide

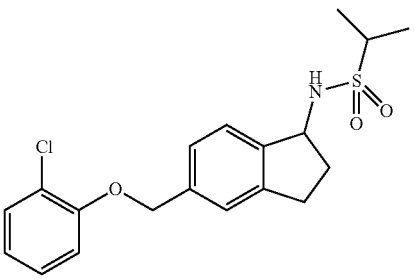 [SMILES: CC(C)S(=O)(=O)NC1CCc2cc(COc3ccccc3Cl)ccc21]

The title compound was prepared using the procedure detailed in Example 37 using 2-chlorophenol instead of 2-(trifluoromethyl)phenol (25 mg, 63.1%). MS (ESI): m/z [M−H]− 378.0

EXAMPLE 39

N-(5-((2-cyanophenoxy)methyl)-2,3-dihydro-1H-inden-1-yl)propane-2-sulfonamide

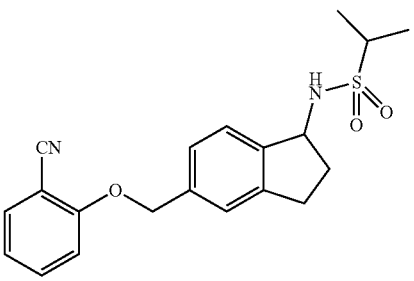 [SMILES: CC(C)S(=O)(=O)NC1CCc2cc(COc3ccccc3C#N)ccc21]

The title compound was prepared using the procedure detailed in Example 37 using 2-hydroxybenzonitrile instead of 2-(trifluoromethyl)phenol (25 mg, 64.7%). MS (ESI): m/z [M−H]⁻ 369.0

EXAMPLE 40

N-(5-((2-bromophenoxy)methyl)-2,3-dihydro-1H-inden-1-yl)propane-2-sulfonamide

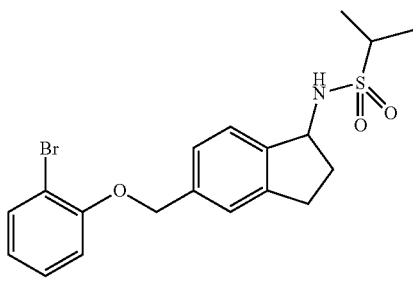 [SMILES: CC(C)S(=O)(=O)NC1CCc2cc(COc3ccccc3Br)ccc21]

The title compound was prepared using the procedure detailed in Example 37 using 2-hydroxybenzonitrile instead of 2-(trifluoromethyl)phenol (38 mg, 86%). MS (ESI): m/z [M−H]⁻ 423.0

EXAMPLE 41

N-(5-(3-(hydroxymethyl)-5-(trifluoromethyl)benzyl)-2,3-dihydro-1H-inden-1-yl)thiophene-2-sulfonamide a) benzyl 5-bromo-2,3-dihydro-1H-inden-1-ylcarbamate,

To a vigorously stirred solution of 5-bromo-2,3-dihydro-1H-inden-1-amine (8.54 g, 40.3 mmol) and potassium carbonate (11.1 g, 80 mmol) in water (100 mL) and ethyl acetate (100 mL) was added benzyl chloroformate (7.56 g, 44.3 mmol). The reaction was stirred at rt overnight before being diluted with water (200 mL) and dichloromethane (200 mL). The organic phase was collected and the aqueous phase was extracted once more with dichloromethane (100 mL). The clear colourless organic layers were dried over sodium sulfate, filtered, and concentrated under reduced pressure to afford a white solid. The material was co-evaporated once with diethyl ether and the residue was triturated with diethyl ether. The white solid was collected by filtration and dried on air to afford the title compound as a white solid (11.5 g, 82%). MS (ESI): m/z [M+H]⁺ 347.0 b) methyl 1-(benzyloxycarbonylamino)-2,3-dihydro-1H-indene-5-carboxylate

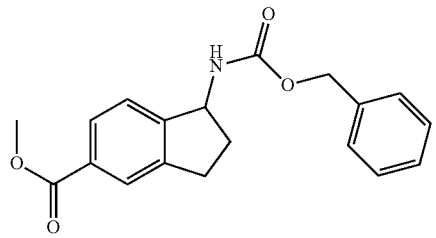 [SMILES: COC(=O)c1ccc2c(c1)CCC2NC(=O)OCc1ccccc1]

A 500 mL steel autoclave was charged with benzyl 5-bromo-2,3-dihydro-1H-inden-1-ylcarbamate (7.50 g, 21.7 mmol), PdCl₂(dppf) (890 mg, 1.1 mmol), and sodium carbonate (4.69 g, 44.3 mmol) in degassed DMF (50 mL) and methanol (50 mL). The autoclave was placed under carbon monoxide (12 bar) and stirred at 100° C. for 3 days. The reaction was cooled to rt, diluted with EtOAc (200 mL) and brine (200 mL), and filtered over Kiezelguhr gel. The organics were isolated and washed with brine (2×200 mL). The organic phase was dried over sodium sulfate, filtered, and concentrated under reduced pressure to afford aa brown oil. This material was purified by flash column chromatography (300 g silica, EtOac/heptane, from 0% to 50% of EtOAc) to the title compound as a white solid (3.87 g, 52.2%). MS (ESI): m/z [M+H]⁺ 326.0 c) benzyl 5-(hydroxymethyl)-2,3-dihydro-1H-inden-1-ylcarbamate

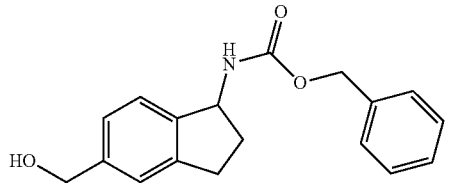 [SMILES: O=C(NC1CCc2cc(CO)ccc21)OCc1ccccc1]

At 0° C., LiAlH₄ (2.4 M, 5.2 mL, 12.5 mmol) was added gradually to a solution of methyl 1-(benzyloxycarbonylamino)-2,3-dihydro-1H-indene-5-carboxylate (3.87 g, 11.9 mmol) in anhydrous THF (50 mL). The reaction was stirred for 1.5 h before being quenched by sequentially adding of water (450 μL), of 1 N NaOH (450 μL), and water (900 μL). The mixture was stirred for 10 minutes. Sodium sulfate was added and the mixture was filtered to remove insoluble salts. The residue was washed with ethyl acetate. The combined organic filtrates were evaporated to dryness in vacuo. The off-white residue was triturated with diethyl ether to afford the title compound as an off white solid (2.53 g, 71.5%). MS (ESI): m/z [M+NH₄]⁺ 315.0 d) benzyl 5-(chloromethyl)-2,3-dihydro-1H-inden-1-ylcarbamate

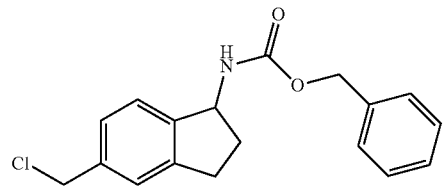 [SMILES: O=C(NC1CCc2cc(CCl)ccc21)OCc1ccccc1]

Thionyl chloride (2.0 g, 16.8 mmol) was added to a suspension of benzyl 5-(hydroxymethyl)-2,3-dihydro-1H-inden-1-ylcarbamate (2.53 g, 8.5 mmol) in DCM (35 mL). The solution was stirred at rt for 1 h before the reaction mixture was evaporated to dryness in vacuo and the material was co-evaporated with diethyl ether (2×100 mL) to afford the title compound as a white solid (2.63 g, 98%). MS (ESI): m/z [M+NH$_4$]$^+$ 333.2 e) methyl 3-((1-(benzyloxycarbonylamino)-2,3-dihydro-1H-inden-5-yl)methyl)-5-(trifluoromethyl)benzoate

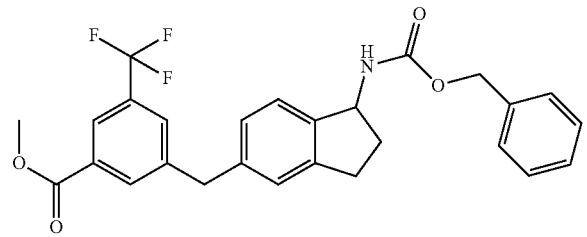 [SMILES: COC(=O)c1cc(Cc2ccc3c(c2)CCC3NC(=O)OCc2ccccc2)cc(C(F)(F)F)c1]

A mixture of benzyl 5-(chloromethyl)-2,3-dihydro-1H-inden-1-ylcarbamate (2.10 g, 6.7 mmol), methyl 3-(5,5-dimethyl-1,3,2-dioxaborinan-2-yl)-5-(trifluoromethyl)benzoate (2.21 g, 7.0 mmol), trans-Bromo(N-succinimidyl)bis(triphenylphosphine)palladium(II) (269 mg, 0.3 mmol), and sodium carbonate (3.52 g, 33.2 mmol) in degassed THF (40 mL) and water (20 mL) was stirred at 80° C. After 3 h the reaction was cooled to rt and diluted with ethyl acetate (200 mL) and washed with brine (2×200 mL). The aqueous phases were extracted once more with ethyl acetate (1×100 mL). The combined organic extracts were dried over sodium sulfate, filtered, and concentrated under reduced pressure to afford a grey solid. The material was purified by silica flash column chromatography (100 g silica, EtOAc/heptane, from 0% to 25% of EtOAc) to afford the title compound as a white solid (2.8 g, 87%). MS (ESI): m/z [M+NH$_4$]$^+$ 501.2.

f) benzyl 5-(3-(hydroxymethyl)-5-(trifluoromethyl)benzyl)-2,3-dihydro-1H-inden-1-yl carbamate

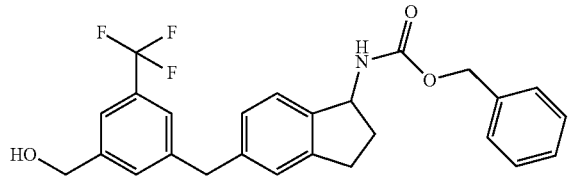 [SMILES: O=C(NC1CCc2cc(Cc3cc(CO)cc(C(F)(F)F)c3)ccc21)OCc1ccccc1]

At 0° C., LiAlH$_4$ (2.4 M, 1.4 mL, 3.4 mmol) was added gradually to a solution of methyl 3-((1-(benzyloxycarbonylamino)-2,3-dihydro-1H-inden-5-yl)methyl)-5-(trifluoromethyl)benzoate (1.53 g, 3.2 mmol) in anhydrous THF (20 mL). The reaction was stirred for 1.5 h before being quenched by sequentially adding of water (120 µL), of 2 N NaOH (120 µL), and of water (240 µL). The mixture was stirred for 10 minutes. Magnesium sulfate was added and the mixture was filtered to remove insoluble salts. The residue was washed with ethyl acetate. The combined organic filtrates were evaporated to dryness in vacuo. The off-white residue was triturated with diethyl ether to afford after filtration the title compound as an off white solid (1.04 g, 72.2%). MS (ESI): m/z [M+NH$_4$]$^+$ 473.2.

g) (3-((1-amino-2,3-dihydro-1H-inden-5-yl)methyl)-5-(trifluoromethyl)phenyl)methanol

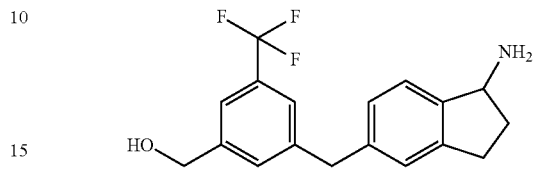

A mixture of benzyl 5-(3-(hydroxymethyl)-5-(trifluoromethyl)benzyl)-2,3-dihydro-1H-inden-1-ylcarbamate (1.04 g, 2.28 mmol) and 10% palladium on carbon (38 mg) in ethanol (20 mL) was placed under hydrogen (balloon) and stirred at rt for 1 h. The mixture was filtered over Celite and concentrated under reduced pressure. The white solid was triturated with diethyl ether to afford the title compound as a white solid (660 mg, 90%). MS (ESI): m/z [M+NH$_2$]$^+$ 305.2 h) N-(5-(3-(hydroxymethyl)-5-(trifluoromethyl)benzyl)-2,3-dihydro-1H-inden-1-yl)thiophene-2-sulfonamide

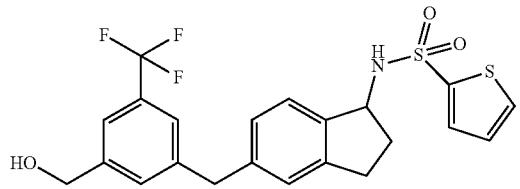

2-thiophenesulfonyl chloride (23 mg, 0.126 mmol) was added to a solution of (3-((1-amino-2,3-dihydro-1H-inden-5-yl)methyl)-5-(trifluoromethyl)phenyl)methanol (40 mg, 0.124 mmol) and triethylamine (34 µL, 0.244 mmol) in DCM (2 mL). The reaction was stirred at rt for 24 h before aq. sat. NaHCO$_3$ (2 mL) was added to the mixture and the whole was filtered over a phase separator. The organic filtrate was evaporated to dryness in a Genevac. The crude material was purified by prep. LCMS to afford the title compound (20.8 mg, 35.7%). MS (ESI): m/z [M−H]$^−$ 466.0.

EXAMPLE 42

N-(5-(3-(hydroxymethyl)-5-(trifluoromethyl)benzyl)-2,3-dihydro-1H-inden-1-yl)furan-2-sulfonamide

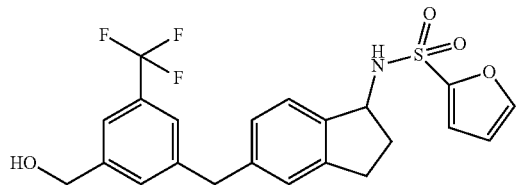 [SMILES: O=S(=O)(NC1CCc2cc(Cc3cc(CO)cc(C(F)(F)F)c3)ccc21)c1cccs1]

The title compound was prepared using the procedure detailed in Example 41h using Furan-2-sulfonyl chloride instead of 2-thiophenesulfonyl chloride (19.7 mg, 35.1%). MS (ESI): m/z [M−H]− 450.0

EXAMPLE 43

N-(5-(3-(hydroxymethyl)-5-(trifluoromethyl)benzyl)-2,3-dihydro-1H-inden-1-yl)cyclopropanesulfonamide

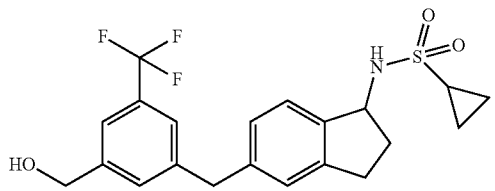 [SMILES: O=S(=O)(NC1CCc2cc(Cc3cc(CO)cc(C(F)(F)F)c3)ccc21)C1CC1]

The title compound was prepared using the procedure detailed in Example 41h using cyclopropanesulfonyl chloride instead of 2-thiophenesulfonyl chloride (17.6 mg, 33.2%). MS (ESI): m/z [M+NH$_4$]+ 443.0

EXAMPLE 44

N-(5-(3-(hydroxymethyl)-5-(trifluoromethyl)benzyl)-2,3-dihydro-1H-inden-1-yl)N,N-dimethylsulfonylurea

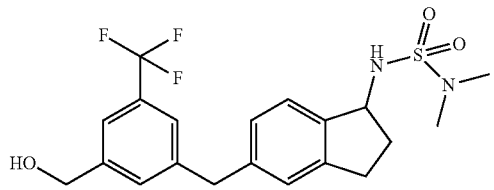 [SMILES: CN(C)S(=O)(=O)NC1CCc2cc(Cc3cc(CO)cc(C(F)(F)F)c3)ccc21]

The title compound was prepared using the procedure detailed in Example 41h using N,N-dimethylsulfamoyl chloride instead of 2-thiophenesulfonyl chloride (8.6 mg, 16.2%). MS (ESI): m/z [M+H]+ 429.0

EXAMPLE 45

N-(5-(3-(hydroxymethyl)-5-(trifluoromethyl)benzyl)-2,3-dihydro-1H-inden-1-yl)-1-methyl-3-(trifluoromethyl)-1H-pyrazole-4-sulfonamide

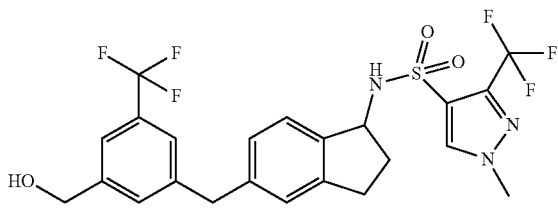 [SMILES: Cn1cc(S(=O)(=O)NC2CCc3cc(Cc4cc(CO)cc(C(F)(F)F)c4)ccc32)c(C(F)(F)F)n1]

The title compound was prepared using the procedure detailed in Example 41h using 1-methyl-3-(trifluoromethyl)-1H-pyrazole-4-sulfonyl chloride instead of 2-thiophenesulfonyl chloride (21.1 mg, 30.8%). MS (ESI): m/z [M+H]+ 534.0

EXAMPLE 46

2,2,2-trifluoro-N-(5-(3-(hydroxymethyl)-5-(trifluoromethyl)benzyl)-2,3-dihydro-1H-inden-1-yl)acetamide

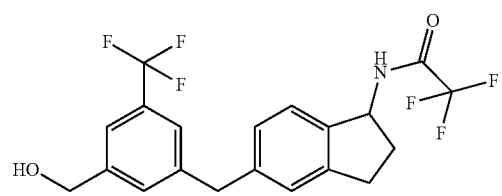 [SMILES: O=C(NC1CCc2cc(Cc3cc(CO)cc(C(F)(F)F)c3)ccc21)C(F)(F)F]

Pentafluorophenyl trifluoroacetate (28 mg, 0.1 mmol) was added to a solution of (3-((1-amino-2,3-dihydro-1H-inden-5-yl)methyl)-5-(trifluoromethyl)phenyl)methanol (30 mg, 0.093 mmol) and triethylamine (26 μL, 0.187) in DCM (1 mL). The reaction was stirred at rt for 24 h before aq. sat. NaHCO$_3$ (2 mL) was added to the mixture and the whole was filtered over a phase separator. The organic filtrate was evaporated to dryness in a Genevac. The crude material was purified by prep. LCMS to afford LEBE27-031-2 the title compound (10.3 mg, 27.7%). MS (ESI): m/z [M−H]− 416.0

EXAMPLE 47

(3-(trifluoromethyl)-5-((1-((3-(trifluoromethyl)pyridin-2-yl)methylamino)-2,3-dihydro-1H-inden-5-yl)methyl)phenyl)methanol

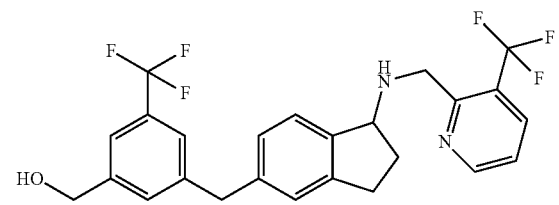 [SMILES: OCc1cc(Cc2ccc3c(c2)CCC3NCc2ncccc2C(F)(F)F)cc(C(F)(F)F)c1]

Sodium triacetoxyborohydride (40 mg, 0.19 mmol) was added to a solution of (3-((1-amino-2,3-dihydro-1H-inden-5-yl)methyl)-5-(trifluoromethyl)phenyl)methanol (30 mg, 0.093) and 3-trifluoromethyl-2-formylpyridine (15 mg, 0.086 mmol) in DCM (1 mL). The reaction was stirred at rt for 24 h before aq. sat. NaHCO$_3$ (2 mL) was added to the mixture was filtered over a phase separator. The organic filtrate was evaporated to dryness in a Genevac. The crude material was purified by prep. LCMS to afford the title compound (18.9 mg, 42.1%). MS (ESI): m/z [M+H]+ 481.2

EXAMPLE 48

(S)-N-(5-(3-(hydroxymethyl)-5-(trifluoromethyl)benzyl)-2,3-dihydro-1H-inden-2-yl)-1-methyl-3-(trifluoromethyl)-1H-pyrazole-4-sulfonamide a) (S)-benzyl 5-bromo-2,3-dihydro-1H-inden-2-ylcarbamate

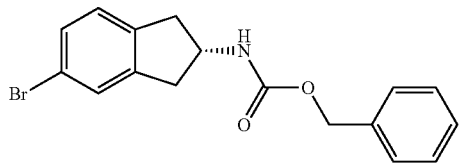 [SMILES: O=C(N[C@H]1Cc2ccc(Br)cc2C1)OCc1ccccc1]

To (S)-5-bromo-2,3-dihydro-1H-inden-2-amine((1R,4S)-7,7-dimethyl-2-oxobicyclo[2.2.1]heptan-1-yl)methanesulfonate (13.95 mmol, 6.2 g) in EtOAc (93 mL)/Water (93 mL) was added benzyl carbonochloridate (15.35 mmol, 2.62 g) dropwise at 0° C. under an argon atmosphere. The reaction was left to stir for 18 hrs. The aqueous layer was removed before washing the organic with brine. The organics were dried over MgSO$_4$ before filtering and removing the solvent in vacuo to give the title compound as a white solid (4.8 g, 99%). $^1$H NMR (400 MHz, CDCl$_3$) δ 2.79 (m, 2H), 3.25 (m, 2H), 4.53 (d, 1H), 4.93 (brs, 1H), 5.10 (s, 2H), 7.08 (d, 1H) 7.31 (m, 7H).

b) (S)-methyl 2-(benzyloxycarbonylamino)-2,3-dihydro-1H-indene-5-carboxylate

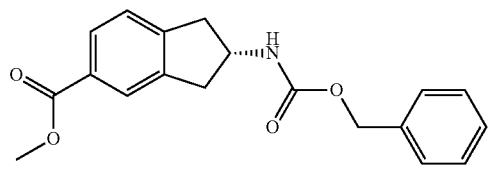 [SMILES: COC(=O)c1ccc2c(c1)C[C@@H](NC(=O)OCc1ccccc1)C2]

To a large CEM microwave vial was added (S)-benzyl 5-bromo-2,3-dihydro-1H-inden-2-ylcarbamate (1.13 g, 3.25 mmol) in Acetonitrile (9 mL)/MeOH (9 mL) was added trans-di-μ-acetatobis[2-(di-O-tolylphosphino)benzyl]dipalladium (II) (0.305 g, 0.325 mmol), tri-tert-butylphosphine tetrafluoroborate (0.189 g. 0.65 mmol), molybdenum hexacarbonyl (0.86 g, 3.25 mmol) and 1,8-diazabicyclo[5.4.0]undec-7-ene (0.74 g, 4.88 mmol). The reaction mixture was heated to 150 degrees for 30 mins. This was repeated with a further 3 batches. The contents of the four reaction vials were combined before removing the solvent in vacuo and redissolving DCM. The DCM layer was washed with 1M HCl (aq), water and then brine. The organics were dried over MgSO$_4$ before removing the solvent in vacuo. The crude material was purified by silica column chromatography (100 g of silica, DCM) to give the title compound as an off-white solid (2.4 g, 56.8%). $^1$H NMR (400 MHz, CDCl$_3$) δ 2.85 (m, 2H), 3.35 (m, 2H), 3.90 (s, 3H), 4.53 (d, 1H), 4.95 (brs, 1H), 5.12 (s, 2H), 7.27 (d, 1H) 7.34 (m, 5H), 7.88 (m, 2H).

c) (S)-benzyl 5-(hydroxymethyl)-2,3-dihydro-1H-inden-2-ylcarbamate

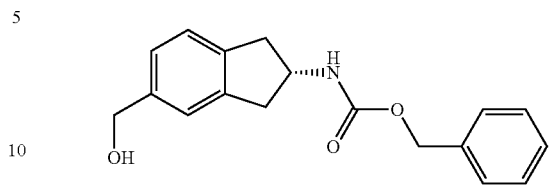

To (S)-methyl 2-(benzyloxycarbonylamino)-2,3-dihydro-1H-indene-5-carboxylate (7.38 mmol, 2.4 g) at 0° C. in THF (36.9 mL) under an argon atmosphere was added Lithium aluminium hydride in THF (7.38 mmol, 7.38 mL) dropwise. The reaction was left to stir for 1.5 hrs at 0 degrees. The reaction was quenched with water before the addition of 5N HCl (aq) to adjust the pH to 3. DCM was added before separating the aqueous and washing once with water and once with brine. The DCM layer was dried over MgSO$_4$ before removing the solvent in vacuo. The crude product was purified by silica chromatography (2:1 Heptane/EtOAc to 2:1 EtOAc/Heptane, 100 g silica cartridge) to give the product as a white solid (1.8 g, 82%). $^1$H NMR (400 MHz, CDCl$_3$) δ 1.60 (t, 1H), 2.81 (m, 2H), 3.27 (m, 2H), 4.53 (d, 1H), 4.66 (d, 2H), 4.95 (brs, 1H), 5.12 (s, 2H), 7.17 (d, 2H), 7.23 (m, 1H), 7.33 (m, 5H).

d) (S)-benzyl 5-(chloromethyl)-2,3-dihydro-1H-inden-2-ylcarbamate

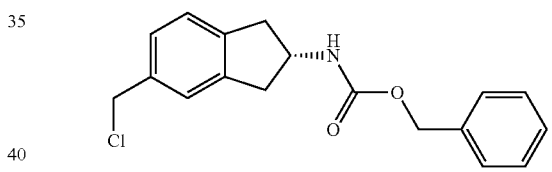

To (S)-benzyl 5-(hydroxymethyl)-2,3-dihydro-1H-inden-2-ylcarbamate (5.72 mmol, 1.7 g) was added DCM (34.9 mL) followed by sulfurous dichloride (11.43 mmol, 1.360 g). The reaction was stirred for one hour before removing the solvent in vacuo. DCM was added (5 mL) before removing the solvent in vacuo, this procedure was followed a further twice to give a yellow solid (1.8 g, 100%). $^1$H NMR (400 MHz, CDCl$_3$) δ 2.81 (m, 2H), 3.30 (m, 2H), 4.56 (m, 3H), 4.95 (brs, 1H), 5.12 (s, 2H), 7.19 (d, 2H), 7.25 (m, 1H), 7.33 (m, 5H).

e) (S)-methyl 3-((2-(benzyloxycarbonylamino)-2,3-dihydro-1H-inden-5-yl)methyl)-5-(trifluoromethyl)benzoate

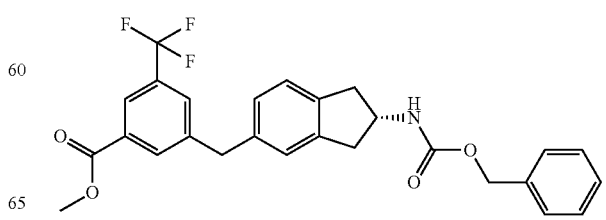

To (S)-benzyl 5-(chloromethyl)-2,3-dihydro-1H-inden-2-ylcarbamate (7.09 mmol, 2.24 g) in THF (44.9 mL) was added methyl 3-(5,5-dimethyl-1,3,2-dioxaborinan-2-yl)-5-(trifluoromethyl)benzoate (7.09 mmol, 2.242 g), Bromo(N-succinimidyl)bis-(triphenylphosphine)palladium(II) (0.355 mmol, 0.287 g) and sodium carbonate (45.0 mmol, 22.5 mL). The reaction was heated to 80° C. for 4 hrs. DCM was added before washing with water (×1) followed by brine (×1). The organics were dried over MgSO₄ before removing the solvent in vacuo. The crude material was purified by silica chromatography (5:1>2:1, hep EtOAc). The solvent was removed to give the title compound as a white solid (2.6 g, 76%). MS (ESI): m/z [M+H]⁺ 484.2 f) (S)-benzyl 5-(3-(hydroxymethyl)-5-(trifluoromethyl)benzyl)-2,3-dihydro-1H-inden-2-ylcarbamate

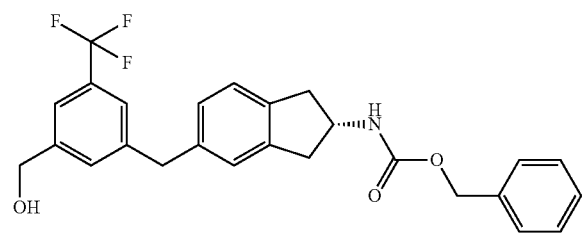 [SMILES: O=C(N[C@H]1Cc2ccc(Cc3cc(CO)cc(C(F)(F)F)c3)cc2C1)OCc1ccccc1]

To (S)-methyl 3-((2-(benzyloxycarbonylamino)-2,3-dihydro-1H-inden-5-yl)methyl)-5-(trifluoromethyl)benzoate (2.90 mmol, 1.4 g) at 0° C. in THF (29.0 mL) under an argon atmosphere was added Lithium aluminium hydride in THF (2.90 mmol, 2.90 mL) dropwise. The reaction was left to stir for 1.5 hrs at 0° C. The reaction was quenched with MeOH before the addition of 5N HCl (aq) to adjust the pH to 3. The reaction mix was diluted with DCM before washing with water (×1) followed by brine (×1). The DCM layer was dried over MgSO4 before removing the solvent in vacuo to give the product as a clear glassy solid (1.34 g, 102%). MS (ESI): m/z [M+H]⁺ 456.1 g) (S)-(3-((2-amino-2,3-dihydro-1H-inden-5-yl)methyl)-5-(trifluoromethyl)phenyl)methanol

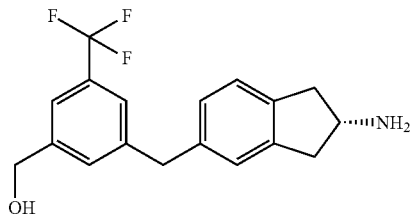 [SMILES: N[C@H]1Cc2ccc(Cc3cc(CO)cc(C(F)(F)F)c3)cc2C1]

To (S)-benzyl 5-(3-(hydroxymethyl)-5-(trifluoromethyl)benzyl)-2,3-dihydro-1H-inden-2-ylcarbamate (2.94 mmol, 1.34 g) in Ethanol (35.4 mL) was added palladium hydroxide (2.51 mmol, 0.353 g). The reaction was placed under 2 bar of hydrogen gas and allowed to stir at room temp for 30 mins. The reaction mix was filtered through a dicalite cartridge before washing with EtOH. The solvent was removed before purifying further by SCX (20 g cartridge, 1:1 MeOH/DCM wash, 2M NH₃ MeOH elution). The solvent was removed to give the product as a clear gum (810 mg, 86%). MS (ESI): m/z [M+H]⁺ 322.2 h) (S)-N-(5-(3-(hydroxymethyl)-5-(trifluoromethyl)benzyl)-2,3-dihydro-1H-inden-2-yl)-1-methyl-3-(trifluoromethyl)-1H-pyrazole-4-sulfonamide

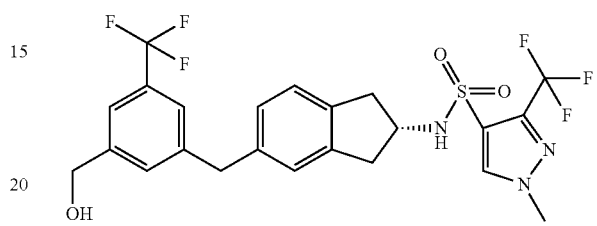

To (S)-(3-((2-amino-2,3-dihydro-1H-inden-5-yl)methyl)-5-(trifluoromethyl)phenyl)methanol (25 mg, 0.078 mmol) in DCM was added triethylamine (22 µL, 0.16 mmol). The sulfonyl chloride was added (19.3 mg, 0.078 mmol) before leaving the reaction to shake overnight (18 hrs). The reaction was quenched with sodium hydrogen carbonate (aq) before separating through a hydrophobic frit. The solvent was removed in vacuo before redissolving in DMSO (500 µL) and purifying by reverse phase preparative chromatography to give the product as a clear film (17.9 mg, 43%). MS (ESI): m/z [M+NH₄]⁺ 551.0

EXAMPLE 49

(S)-N-(5-(3-(hydroxymethyl)-5-(trifluoromethyl)benzyl)-2,3-dihydro-1H-inden-2-yl)-N,N-dimethylsulfonylurea

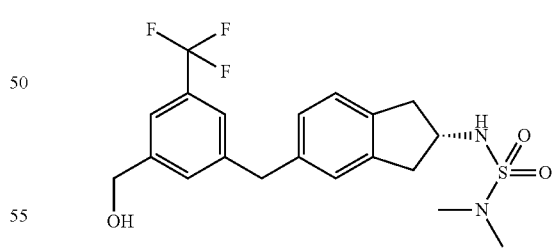

To (S)-(3-((2-amino-2,3-dihydro-1H-inden-5-yl)methyl)-5-(trifluoromethyl)phenyl)methanol (0.093 mmol, 30 mg) in DCM (1 mL) was added triethylamine (0.187 mmol, 18.89 mg) followed by dimethylsulfamoyl chloride (0.093 mmol, 13.41 mg). The reaction was left to stir for 7 days before removing the solvent in vacuo and redissolving in DMSO. The DMSO solution was purified by reverse phase preparative HPLC to give the title compound as a clear gum (16.4 mg, 41.0%). MS (ESI): m/z [M+H]⁺ 429.0

EXAMPLE 50

(S)-N-(5-(3-(hydroxymethyl)-5-(trifluoromethyl)benzyl)-2,3-dihydro-1H-inden-2-yl)methanesulfonamide

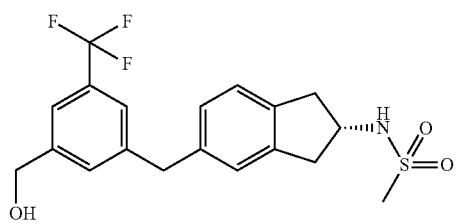 [SMILES: CS(=O)(=O)N[C@H]1Cc2ccc(Cc3cc(CO)cc(C(F)(F)F)c3)cc2C1]

To (S)-(3-((2-amino-2,3-dihydro-1H-inden-5-yl)methyl)-5-(trifluoromethyl)phenyl)methanol (50, mg, 0.16 mmol) in THF (1 mL) was added perfluorophenyl methanesulfonate (39 mg, 0.15 mmol) followed by 2,3,4,6,7,8,9,10-octahydropyrimido[1,2-a]azepine (34.1 mg 0.22 mmol). The reaction was allowed to stir at RT overnight before removing the solvent in vacuo. The sample was redissolved in DMSO (500 µL) before purifying by reverse phase preparative HPLC-MS to give the title compound as a clear film (11 mg, 17.2%). MS (ESI): m/z [M+H]$^+$ 400.1

EXAMPLE 51

(S)-N-(5-((2-(trifluoromethyl)phenoxy)methyl)-2,3-dihydro-1H-inden-2-yl)propane-2-sulfonamide

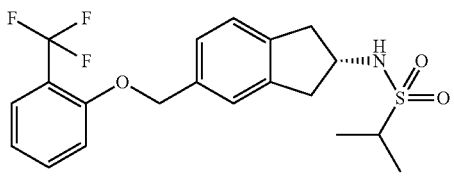 [SMILES: CC(C)S(=O)(=O)N[C@H]1Cc2ccc(COc3ccccc3C(F)(F)F)cc2C1]

A mixture of potassium carbonate (0.174 mmol, 24.01 mg), 2-(trifluoromethyl)phenol (0.087 mmol, 14.08 mg), and (S)-N-(5-(chloromethyl)-2,3-dihydro-1H-inden-2-yl)propane-2-sulfonamide (0.087 mmol, 25 mg) in DMF (2 mL) was heated at 120° C. for 900 s in a Smith Synthesiser microwave. The reaction mixture was concentrated to dryness before DCM (2 mL) and H$_2$O (2 mL) was added and the reaction mixture filtered through a hydrophobic frit washing with further DCM (2 mL). The DCM layer was concentrated to dryness and purified by preparative HPLC to furnish the desired product (10.0 mg, 27.8%). MS (ESI): m/z [M−H]$^-$ 412.2

EXAMPLE 52

(S)-N-(5-((2-chloropyridin-3-yloxy)methyl)-2,3-dihydro-1H-inden-2-yl)propane-2-sulfonamide

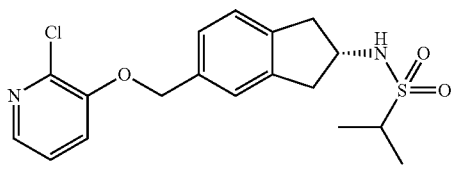 [SMILES: CC(C)S(=O)(=O)N[C@H]1Cc2ccc(COc3cccnc3Cl)cc2C1]

The title compound was prepared using the procedure detailed in Example 51 using 2-chloropyridin-3-ol instead of 2-(trifluoromethyl)phenol (5.8 mg, 17.5%). MS (ESI): m/z [M−H]$^-$ 379.0

EXAMPLE 53

(S)-N-(5-((2-bromophenoxy)methyl)-2,3-dihydro-1H-inden-2-yl)propane-2-sulfonamide

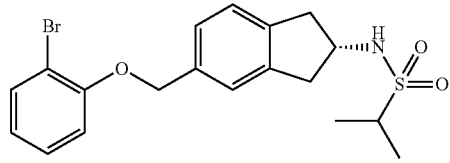 [SMILES: CC(C)S(=O)(=O)N[C@H]1Cc2ccc(COc3ccccc3Br)cc2C1]

The title compound was prepared using the procedure detailed in Example 51 using 2-bromophenol instead of 2-(trifluoromethyl)phenol (7.5 mg, 20.4%). MS (ESI): m/z [M−H]$^-$ 424.0

EXAMPLE 54

(S)-N-(5-((2-(trifluoromethoxy)phenoxy)methyl)-2,3-dihydro-1H-inden-2-yl)propane-2-sulfonamide

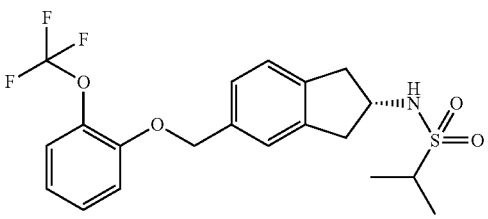 [SMILES: CC(C)S(=O)(=O)N[C@H]1Cc2ccc(COc3ccccc3OC(F)(F)F)cc2C1]

The title compound was prepared using the procedure detailed in Example 51 using 2-(trifluoromethoxy)phenol instead of 2-(trifluoromethyl)phenol (10.7 mg, 28.7%). MS (ESI): m/z [M−H]$^-$ 428.0

EXAMPLE 55

(S)-N-(5-((2-fluorophenoxy)methyl)-2,3-dihydro-1H-inden-2-yl)propane-2-sulfonamide

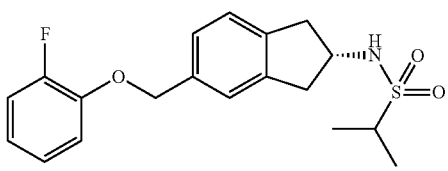 [SMILES: CC(C)S(=O)(=O)N[C@H]1Cc2ccc(COc3ccccc3F)cc2C1]

The title compound was prepared using the procedure detailed in Example 51 using 2-fluorophenol instead of 2-(trifluoromethyl)phenol (10.7 mg, 28.7%). MS (ESI): m/z [M–H]⁻ 362.0

EXAMPLE 56

(S)-44 (2-(1-methylethylsulfonamido)-2,3-dihydro-1H-inden-5-yl)methoxy)benzamide

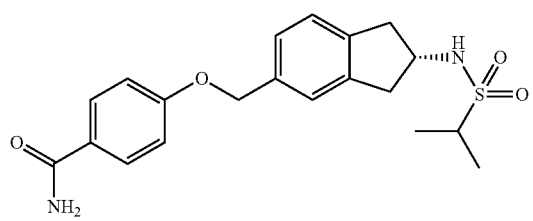 [SMILES: CC(C)S(=O)(=O)N[C@H]1Cc2ccc(COc3ccc(C(N)=O)cc3)cc2C1]

The title compound was prepared using the procedure detailed in Example 51 using 4-hydroxybenzamide instead of 2-(trifluoromethyl)phenol (9.5 mg, 28.2%). MS (ESI): m/z [M–H]⁻ 387.3

EXAMPLE 57

(S)-N-(5-(2-cyanobenzyloxy)-2,3-dihydro-1H-inden-2-yl)propane-2-sulfonamide

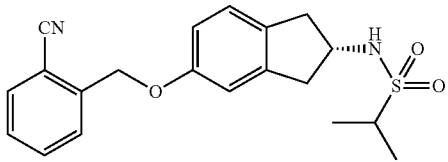 [SMILES: CC(C)S(=O)(=O)N[C@H]1Cc2ccc(OCc3ccccc3C#N)cc2C1]

A mixture of (S)-N-(5-hydroxy-2,3-dihydro-1H-inden-2-yl)propane-2-sulfonamide (0.098 mmol, 25 mg) and NaH (0.196 mmol, 4.70 mg) in DMF (1 mL) was stirred at room temp for 15 min. 2-(bromomethyl)benzonitrile (0.098 mmol, 19.20 mg) in DMF (1 mL) was added and the reaction mixture heated at 120° C. for 600 s in a Smith Synthesiser microwave. The reaction mixture was filtered through a Whatman filter and purified by preparative HPLC to give desired product (17.8 mg, 49.1%). MS (ESI): m/z [M–H]⁻ 369.2

EXAMPLE 58

(S)-N-(5-(2-(difluoromethoxy)benzyloxy)-2,3-dihydro-1H-inden-2-yl)propane-2-sulfonamide

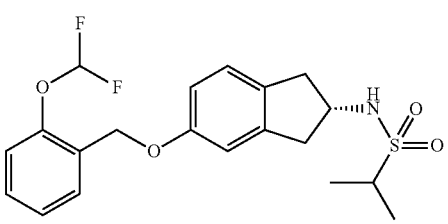 [SMILES: CC(C)S(=O)(=O)N[C@H]1Cc2ccc(OCc3ccccc3OC(F)F)cc2C1]

The title compound was prepared using the procedure detailed in Example 57 using 1-(bromomethyl)-2-(difluoromethoxy)benzene instead of 2-(bromomethyl)benzonitrile (2.7 mg, 3.4%). MS (ESI): m/z [M–H]⁻ 410.0

EXAMPLE 59

(S)-N-(5-(2-(trifluoromethoxy)benzyloxy)-2,3-dihydro-1H-inden-2-yl)propane-2-sulfonamide

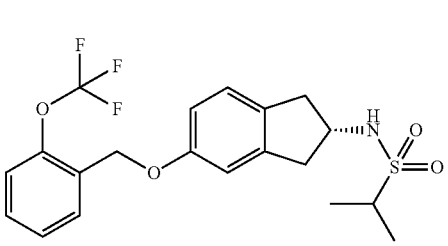 [SMILES: CC(C)S(=O)(=O)N[C@H]1Cc2ccc(OCc3ccccc3OC(F)(F)F)cc2C1]

The title compound was prepared using the procedure detailed in Example 57 using 1-(bromomethyl)-2-(trifluoromethoxy)benzene instead of 2-(bromomethyl)benzonitrile (5.2 mg, 6.2%). MS (ESI): m/z [M–H]⁻ 428.0

EXAMPLE 60

(S)-2-(1-methylethylsulfonamido)-N-(2-(methylsulfonamido)phenyl)-2,3-dihydro-1H-indene-5-carboxamide a) (S)-2-(1-methylethylsulfonamido)-2,3-dihydro-1H-indene-5-carboxylic Acid

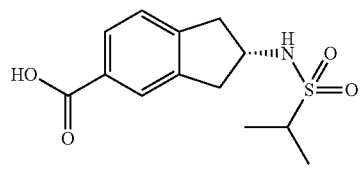 [SMILES: CC(C)S(=O)(=O)N[C@H]1Cc2ccc(C(=O)O)cc2C1]

A mixture of (S)-methyl 2-(1-methylethylsulfonamido)-2,3-dihydro-1H-indene-5-carboxylate (2.320 mmol, 690 mg) and lithium hydroxide (5.10 mmol, 122 mg) in H₂O (25 mL)

and MeOH (25 mL) was stirred at room temp for 2 days. EtOAc was added followed by 2M aq HCl and the reaction mixture extracted with EtOAc (×3). The EtOAc layers were combined and washed with brine, dried over MgSO$_4$, filtered and the solvent removed in vacuo to give desired product as a white solid (514 mg, 78%). MS (ESI): m/z [M−H]⁻ 282.2 b) (S)-2-(1-methylethylsulfonamido)-N-(2-(methylsulfonamido)phenyl)-2,3-dihydro-1H-indene-5-carboxamide

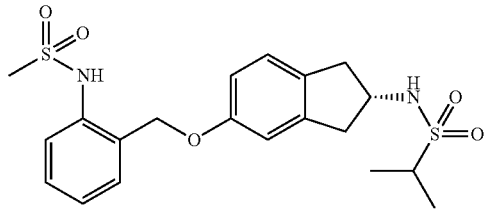 [SMILES: CC(C)S(=O)(=O)N[C@H]1Cc2ccc(OCc3ccccc3NS(C)(=O)=O)cc2C1]

A mixture of (S)-2-(1-methylethylsulfonamido)-2,3-dihydro-1H-indene-5-carboxylic acid (0.088 mmol, 25 mg) and oxalyl chloride (0.441 mmol, 0.038 mL, 56.0 mg) in DCM (5 mL). 1 drop DMF was added and the reaction mixture stirred at room temp for 4 hrs. The reaction mixture was concentrated under reduced pressure before DCM was added and the reaction mixture again concentrated under reduced pressure. This was repeated twice further to give the acid chloride intermediate.

A mixture of triethylamine (0.083 mmol, 0.012 mL, 8.38 mg) and N-(2-aminophenyl)methanesulfonamide (0.083 mmol, 15.43 mg) in DCM (2 mL) was added to a solution of (S)-2-(1-methylethylsulfonamido)-2,3-dihydro-1H-indene-5-carbonyl chloride (0.083 mmol, 25 mg) in DCM (1 mL) was added. The reaction mixture was stirred at room temp overnight. H$_2$O was added and the reaction mixture filtered through a hydrophobic frit and the DCM layer was concentrated under reduced pressure. The residue was purified by prep-HPLC to give desired product (10.7 mg, 28.6%). MS (ESI): [M−H]⁻ 450.2

EXAMPLE 61

(S)-1,1,1-trifluoro-N-(5-(3-(hydroxymethyl)-5-(trifluoromethyl)benzyl)-2,3-dihydro-1H-inden-2-yl)methanesulfonamide a) (S)-methyl 3-((2-amino-2,3-dihydro-1H-inden-5-yl)methyl)-5-(trifluoromethyl)benzoate

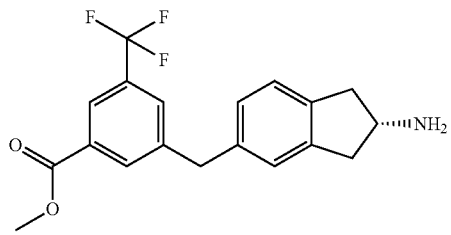 [SMILES: COC(=O)c1cc(Cc2ccc3c(c2)C[C@@H](N)C3)cc(C(F)(F)F)c1]

A suspension of (S)-methyl 3-((2-(benzyloxycarbonylamino)-2,3-dihydro-1H-inden-5-yl)methyl)-5-(trifluoromethyl)benzoate (0.254 mmol, 123 g) and palladium hydroxide (0.064 mmol, 45 mg) in ethanol (9 mL) was treated under hydrogenation conditions (2 bar hydrogen) for 30 minutes. The reaction mixture was filtered through celite and the pad washed with EtOH & EtOAc before the filtrate was concentrated under reduced pressure to give a light brown film (82 mg, 92%). MS (ESI): m/z [M+H]⁺ 350.0 b) (S)-methyl 3-(trifluoromethyl)-5-((2-(trifluoromethylsulfonamido)-2,3-dihydro-1H-inden-5-yl)methyl)benzoate

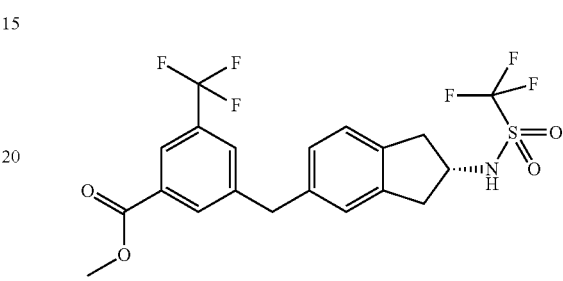

To a solution of (S)-methyl 3-((2-amino-2,3-dihydro-1H-inden-5-yl)methyl)-5-(trifluoromethyl)benzoate (0.235 mmol, 82 mg) and DIPEA (0.469 mmol, 0.078 mL, 60.7 mg) in DCM (2 mL) at 0° C. was added trifluoromethanesulfonic anhydride (0.235 mmol, 0.039 mL, 66.2 mg). The whole was allowed to warm to room temperature overnight with stirring before the reaction mixture was quenched by the addition of 2N HCl & the organics separated through a hydrophobic frit. Following concentration to dryness, the residue was purified by chromatography (20% EtOAc/heptane) to give a white solid (65 mg, 57.5%). MS (ESI): m/z [M+H]⁺ 482.0 c) (S)-1,1,1-trifluoro-N-(5-(3-(hydroxymethyl)-5-(trifluoromethyl)benzyl)-2,3-dihydro-1H-inden-2-yl)methanesulfonamide

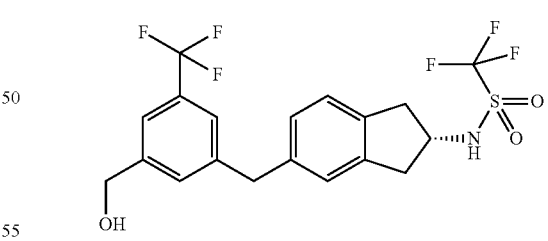

To a solution of (S)-methyl 3-(trifluoromethyl)-5-((2-(trifluoromethylsulfonamido)-2,3-dihydro-1H-inden-5-yl)methyl)benzoate (0.135 mmol, 65 mg) in THF (1.5 mL) at 0° C. was added Lithium aluminium hydride (0.405 mmol, 15.37 mg). The whole was stirred at 0° C. for 4 h before the reaction mixture was quenched by the addition of 2N HCl & diluted with DCM. The organics were separated/dried using a hydrophobic frit before being concentrated to dryness and the residue purified by preparative HPLC to give a clear film (29 mg, 47.4%). MS (ESI): m/z [M+NH$_4$]⁺ 471.5

EXAMPLE 62 a) (R)-5-bromo-2,3-dihydro-1H-inden-2-amine((1S,4R)-7,7-dimethyl-2-oxobicyclo[2.2.1]heptan-1-yl)methanesulfonate

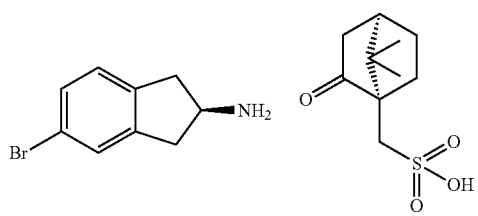

A suspension of 5-bromo-2,3-dihydro-1H-inden-2-amine hydrobromide (107 mmol, 31.38 g) and N-Methylmorpholine (112 mmol, 12.36 mL, 11.37 g) in methanol (66.9 mL) was heated to 58-62° C. and a solution of D-(+)-10-Camphorsulfonic acid (139 mmol, 32.3 g) in Methanol (53.6 mL) was added over 3 min maintaining internal temp at 60-65° C. The addition funnel was rinsed with methanol (13.26 mL) and rinsings added to reaction. The mixture was stirred at for 10 min until a clear solution was obtained. The reaction was then allowed to cool to room temperature and stirred for a total of 4 h. The solids were collected by filtration and washed with a pre-cooled mixture of isopropyl acetate/methanol 2:1 (2×15 mL) followed by water (2×15 mL). The crude product was dried in a vacuum oven at 50° C. overnight to yield (23.1 g) of a fluffy white solid. This was suspended in methanol (160 mL) and heated to reflux for 4 h then allowed to cool to room temperature with stirring over 2 h and stirring continued at room temperature for a further 1 h. Solids were then isolated by filtration and washed with a pre-cooled solution of isopropylacetate/methanol (2:1, 2×18 mL). The colourless solid (15.51 g) was dried in the vacuum oven for 60 h. Refluxing in methanol followed by washing the solid with isopropyl acetate/methanol was repeated until the desired enantiomeric ratio was obtained. (R)-5-bromo-2,3-dihydro-1H-inden-2-amine((1S,4R)-7,7-dimethyl-2-oxobicyclo[2.2.1]heptan-1-yl)methanesulfonate was obtained as a colourless solid (13.83 g, e.e. 100:0, 29.1%). $^1$H NMR (400 MHz, DMSO$_{d6}$) δ 0.72 (s, 3H) 1.04 (s, 3H) 1.28 (m, 2H) 1.80 (m, 2H) 1.94 (m, 1H) 2.25 (m, 1H) 2.38 (m, 1H) 2.69 (m, 1H) 2.83-2.95 (m, 3H) 3.25 (m, integration masked water peak) 4.02 (m, 1H) 7.25 (d, 1H) 7.39 (d, 1H) 7.50 (s, 1H) 8.00 (bs, 3H)

b) (R)-N-(5-bromo-2,3-dihydro-1H-inden-2-yl)propane-2-sulfonamide

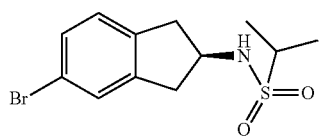 [SMILES: CC(C)S(=O)(=O)N[C@@H]1Cc2ccc(Br)cc2C1]

(R)-5-bromo-2,3-dihydro-1H-inden-2-amine((1S,4R)-7,7-dimethyl-2-oxobicyclo[2.2.1]heptan-1-yl)methanesulfonate (7.88 mmol, 3.5 g) was suspended in DCM (40 mL) and DBU (23.63 mmol, 3.53 mL, 3.60 g) was added. The mixture was purged with nitrogen and cooled in an ice bath before dropwise addition of propane-2-sulfonyl chloride (15.75 mmol, 1.760 mL, 2.246 g). Stirring was continued at 0° C. for 1 h before allowing to come to room temperature. The mixture was diluted with DCM (100 mL) and 1N HCl (100 mL) and the phases mixed and separated. The aqueous phase was further extracted with DCM (2×100 mL) before combined organics were washed with brine. Concentration gave a light yellow oil which was purified on silica eluting with 75% DCM/heptane then neat DCM. Desired fractions were collected and concentrated to give (R)-N-(5-bromo-2,3-dihydro-1H-inden-2-yl)propane-2-sulfonamide as a colourless oil (2.18 g, 87%). $^1$H NMR (400 MHz, CDCl$_3$) δ 1.39 (d, 6H) 2.88 (m, 2H) 3.17 (sept, 1H) 3.28 (m, 2H) 4.27 (m, 2H) 7.08 (d, 1H) 7.30 (d, 1H) 7.35 (s, 1H)

c) (R)-N-(5-(4,4,5,5-tetramethyl-1,3,2-dioxaborolan-2-yl)-2,3-dihydro-1H-inden-2-yl)propane-2-sulfonamide

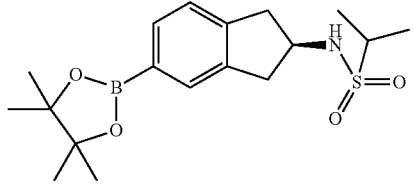 [SMILES: CC(C)S(=O)(=O)N[C@@H]1Cc2ccc(B3OC(C)(C)C(C)(C)O3)cc2C1]

d) (R)-N-(5-hydroxy-2,3-dihydro-1H-inden-2-yl)propane-2-sulfonamide

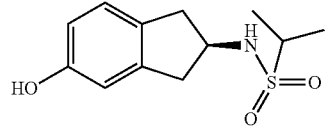 [SMILES: CC(C)S(=O)(=O)N[C@@H]1Cc2ccc(O)cc2C1]

To a stirred solution of (R)-N-(5-(4,4,5,5-tetramethyl-1,3,2-dioxaborolan-2-yl)-2,3-dihydro-1H-inden-2-yl)propane-2-sulfonamide (6.21 mmol, 2.27 g) in acetone (20.00 mL), a solution of oxone monopersulfate compound (6.84 mmol, 4.20 g) in Water (20 mL) was added dropwise over 2 min. The resultant solution was stirred for a further 10 min before being quenched with NaHSO$_3$ (aq). The solution was extracted with DCM (×3), dried (MgSO$_4$), filtered and concentrated in vacuo to give the crude product as a colourless oil which solidified to a white solid on standing. The solid was triturated with heptane to give the title compound as a white solid (1.46 g, 92%). MS (ESI): m/z [M−H]$^-$ 254.0 e) (R)-N-methyl-3-(2-(1-methylethylsulfonamido)-2,3-dihydro-1H-inden-5-yloxy)benzene sulfonamide

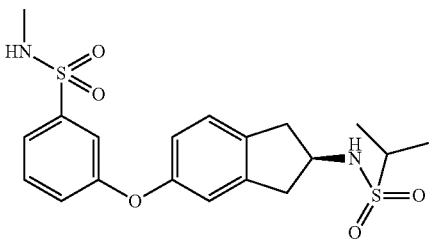 [SMILES: CNS(=O)(=O)c1cccc(Oc2ccc3c(c2)C[C@H](NS(=O)(=O)C(C)C)C3)c1]

To a mixture of the 3-(N-methylsulfamoyl)phenylboronic acid (0.274 mmol, 59 mg), copper (II)acetate (0.137 mmol, 25 mg), triethylamine (0.685 mmol, 96 µL) and 4 Å molecular sieves (100 mg) in DCM (1 mL) was added (R)-N-(5-hydroxy-2,3-dihydro-1H-inden-2-yl)propane-2-sulfonamide (0.137 mmol, 35 mg) and the resultant mixture stirred at room temperature overnight. The reaction mixture was diluted with DCM (1 mL) before water (0.5 mL) was added and the organic layers separated using hydrophobic frits. The aqueous was extracted with further DCM (1 mL), and the combined organics concentrated using to dryness. The residue was taken up in DMSO and purified by preparative HPLC to give the title compound as a clear film (5.9 mg, 10.1%). MS (ESI): m/z [M−H]⁻ 423.2

EXAMPLE 63

(R)-N-(5-(6-(trifluoromethyl)pyridin-2-yloxy)-2,3-dihydro-1H-inden-2-yl)propane-2-sulfonamide

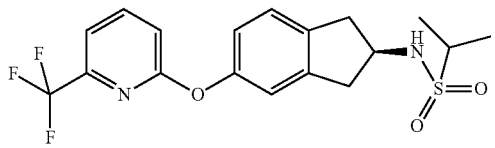 [SMILES: CC(C)S(=O)(=O)N[C@@H]1Cc2ccc(Oc3cccc(C(F)(F)F)n3)cc2C1]

The title compound was prepared using the procedure detailed in Example 62 using 4-(4,4,5,5-tetramethyl-1,3,2-dioxaborolan-2-yl)-2-(trifluoromethyl)pyridine instead of 3-(N-methylsulfamoyl)phenylboronic acid (7.5 mg, 13.7%). MS (ESI): m/z [M−H]⁻ 399.2

EXAMPLE 64

Biological Assays
A: $Ca^{2+}$ Influx Fluorescence Assays

The compounds in this invention may be tested using a biological assay which measures $Ca^{2+}$ influx mediated through positive modulation of the AMPA (GluR1) receptor using standard techniques in the art such as, but not limited to, a FLEXstation (manufactured by Molecular Devices, Sunnyvale, Calif.). An optical readout using fluorescent probes is employed to measure ion channel dependent changes in intracellular ion concentration or membrane potential. The assay utilises the $Ca^{2+}$ conductance of functional homomeric GluR1(i) AMPA receptors to generate glutamate-dependent $Ca^{2+}$ responses. Influx of $Ca^{2+}$ through the ion channel is measured indirectly through an increase in intracellular $Ca^{2+}$ levels using the calcium sensitive dye such as, but not limited to, Fluo-3 (Molecular Devices, Sunnyvale, Calif.) in FLEXstation. A positive AMPA receptor modulator, in the presence of glutamate, will result in an influx of $Ca^{2+}$ through the ion channel which can be measured indirectly through an increase in intracellular Ca2+ levels using the calcium sensitive dye Fluo-3 in FLEXstation.

HEK.GluR1(i) cells were maintained in DMEM supplemented with 10% fetaclone II, 1% non-essential amino acids and 150 µg/mL hygromycin, at 37° C./5% CO2. Twenty-four h prior to the assay, the cells were harvested with trypsin and seeded onto Costar 96 well clear bottomed black plates at a density of 3.5×10⁴ per well.

Cells were loaded with 5 µM fluo3-AM in DMEM media in the absence of hygromycin and incubated at 37° C./5% $CO_2$ for one h. After dye loading, the cells were washed once with 200 µL of low calcium solution (10 mM hepes, pH 7.4, 160 mM NaCl, 4.5 mM KCl, 2 mM $CaCl_2$, 1 mM $MgCl_2$, 10 mM glucose) containing 0.625 mM of probenecid (inhibitor for the anion-exchange protein) to remove the dye. Then 200 µL of low calcium solution was added to each well. The Flexstation added 50 µL of glutamate+/−test compound in high calcium solution (10 mM Hepes, pH 7.4, 160 mM NaCl, 4.5 mM KCl, 20 mM $CaCl_2$, 1 mM $MgCl_2$ and 10 mM glucose) to each well and the ensuing response was monitored on FLEXstation.

The compounds of this invention exhibit positive modulation of the AMPA receptor having $EC_{50}$ values in the range 0.3 µM to 30 µM. For instance, Example 9 gave an $EC_{50}$ of 2.3 µM.
B: Patch Clamp Recording.

The whole cell configuration of the patch clamp technique (Hamill et a/., Pflugers Arch. 1981, 39, 85-100) was used to measure glutamate-evoked currents from postnatal rat cortical neurons. A glass coverslip containing the culture was transferred to the recording chamber (Warner Instrument Corp., Hamden, Conn.) mounted on the stage of an inverted microscope (Nikon, Kingston, UK). The recording chamber contained 1-2 mL extracellular solution (145 mM NaCl, 5.4 mM KCl, 10 mM HEPES, 0.8 mM $MgCl_2$, 1.8 $CaCl_2$, 10 mM glucose and 30 mM sucrose, adjusted to pH 7.4 with 1M NaOH) and was constantly perused at a rate of 1 mL/min. Recordings were performed at room temperature (20-22° C.) using an Axopatch 200B amplifier (Axon Instruments Ltd., Foster City, Calif.).

Data acquisition and analysis was performed using Signal software (Cambridge Electronic Design Ltd., Cambridge, UK). Pipettes were manufactured from GC120E-10 glass (Harvard Apparatus, Edenbridge UK) using a model P-87 electrode puller (Sutter Instruments Co., Novarto, Calif.). The patch electrodes had typical resistances of between 3-5 MQ when filled with intracellular solution (140 mM potassium gluconate, 20 mM HEPES, 1. 1 mM EGTA, 5 mM phosphocreatine, 3 mM ATP, 0.3 mM GTP, 0.1 mM Caca2, 5 mM $MgCl_2$, adjusted to pH 7.4 with 1M KOH).

Cells were voltage clamped at a holding potential of −60 mV and glutamate (0.5 mM) was applied using a 12 channel semi-rapid drug application device (DAD-12. Digitimer Ltd., Welwyn Garden city, UK). The agonist glutamate was applied for 1 s every 30 s. The response did not "run-down" over time using the whole-cell configuration. Between applications saline flowed to clear any dead volume in the system. For each application steady-state currents were plotted from the difference in baseline and steady state current and averaged over 300 ms.

Two solutions of the compound in extracellular solution were made up, one with glutamate and one without. The protocol was: 10 second application of compound, 1 second application of compound+glutamate and then 10 second wash with saline, then a 10 second delay. When the compound was not soluble, 0.5% DMSO was used as a co-solvent. Results are presented in Table I as the percentage increase in steady state current at 10 pM concentration of the compound of the invention in extracellular solution.

The invention claimed is:
1. An indane compound according to formula I

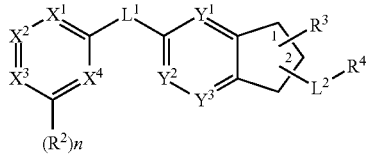

formula I wherein
L$^1$ is O, (CR$^5$R$^6$)$_m$, OCR$^7$R$^8$ or CR$^9$R$^{10}$O;
L$^2$ is NR$^{11}$SO$_2$ or SO$_2$NR$^{12}$;
X$^1$-X$^4$ are CR$^1$;
R$^1$ is H, C$_{1-6}$alkyl, C$_{3-8}$cycloalkyl, C$_{1-6}$alkyloxy, halogen, CN, SC$_{1-6}$alkyl, SOC$_{1-6}$alkyl, SO$_2$C$_{1-6}$alkyl, NR$^{13}$SO$_2$R$^{14}$, CH$_2$NR$^{15}$SO$_2$R$^{16}$, CONR$^{17}$R$^{18}$, NR$^{19}$COR$^{20}$ or SO$_2$NR$^{21}$R$^{22}$,
said C$_{1-6}$alkyl, C$_{3-8}$cycloalkyl and C$_{1-6}$alkyloxy being optionally substituted with one or more halogens with the proviso that each R$^1$ cannot simultaneously be H;
or two R$^1$ together form a fused 5- or 6-membered heteroaryl ring comprising 1-3 heteroatoms independently selected from O, S and N;
R$^2$ is C$_{1-6}$alkyl, C$_{3-8}$cycloalkyl, C$_{1-6}$alkyloxy or CN, said C$_{1-6}$alkyl, C$_{3-8}$cycloalkyl and C$_{1-6}$alkyloxy being substituted with one or more moiety independently selected from OH, C$_{1-6}$alkyloxy and NR$^{23}$R$^{24}$;
R$^3$ is H, C$_{1-6}$alkyl C$_{3-8}$cycloalkyl, C$_{1-6}$alkyloxy, halogen or CN, said C$_{1-6}$alkyl, C$_{3-8}$ cycloalkyl and C$_{1-6}$alkyloxy being optionally substituted with one or more halogens;
R$^4$ is H, C$_{1-6}$alkyl, C$_{2-6}$alkenyl, C$_{2-6}$alkynyl, C$_{3-8}$cycloalkyl, C$_{3-8}$cycloalkylC$_{1-2}$alkyl, NR$^{25}$R$^{26}$, C$_{6-10}$aryl or a 5-9 membered heteroaryl ring system comprising 1-3 heteroatoms independently selected from O, S and N, wherein said C$_{1-6}$alkyl, C$_{3-8}$cycloalkyl, C$_{6-10}$aryl and 5-9 membered heteroaryl ring system are optionally substituted with one or more moieties independently selected from halogen, C$_{1-6}$alkyl, hydroxy and C$_{1-6}$alkyloxy, said C$_{1-6}$alkyl, and C$_{1-6}$alkyloxy being optionally substituted with 1-3 halogens;
R$^5$-R$^{13}$ are independently H or C$_{1-6}$alkyl;
R$^{14}$ and R$^{16}$ are independently C$_{1-6}$alkyl;
R$^{15}$, R$^{17}$, R$^{18}$ and R$^{19}$ are independently H or C$_{1-6}$alkyl;
R$^{20}$ is C$_{1-6}$alkyl;
R$^{21}$ and R$^{22}$ are independently H or C$_{1-6}$alkyl
R$^{23}$ and R$^{24}$ are independently H or C$_{1-4}$alkyl or R$^{23}$ and R$^{24}$ together with the N to which they are bonded form a 4-6 membered saturated or unsaturated heterocyclic ring optionally comprising another heteroatomic moiety selected from O, S and N(R$^{27}$)$_p$;
R$^{25}$ and R$^{26}$ are independently H or C$_{1-4}$alkyl or R$^{25}$ and R$^{26}$ together with the N to which they are bonded form a 4-6 membered saturated or unsaturated heterocyclic ring optionally comprising another heteroatomic moiety selected from O, S and N(R$^{28}$)$_q$;
R$^{27}$ and R$^{28}$ are independently H or C$_{1-4}$alkyl;
m is 1-2;
n is 0 or 1;
p is 0 or 1;
q is 0 or 1;
Y$^1$-Y$^3$ are CR$^{29}$;

R$^{29}$ is H or C$_{1-6}$alkyl optionally substituted with one or more halogens;
or a pharmaceutically acceptable salt or solvate thereof, with the proviso that when L$^1$ is (CR$^5$R$^6$)$_m$ and L$^2$ is a substituent at the 2-position, n cannot be 0.

2. The indane compound according to claim 1 or a pharmaceutically acceptable salt or solvate thereof, wherein R$^1$ is H, Cl, F, CF$_3$, OCF$_3$, CN, SO$_2$CH$_3$, SO$_2$NHCH$_3$, NHSO$_2$CH$_3$ or CH$_2$NHSO$_2$CH$_3$.

3. The indane compound according to claim 1 or a pharmaceutically acceptable salt or solvate thereof, wherein R$^2$ is methyl substituted with hydroxy or NR$^{23}$R$^{24}$, wherein R$^{23}$ and R$^{24}$ have the previously defined meanings.

4. The indane compound according to claim 1 or a pharmaceutically acceptable salt or solvate thereof, wherein R$^3$ is H.

5. The indane compound according to claim 1 or a pharmaceutically acceptable salt or solvate thereof, wherein R$^4$ is ethyl, isopropyl, cyclopropyl, tertiary-butyl or dimethylamino, wherein said ethyl, isopropyl, cyclopropyl and tertiary-butyl are optionally substituted with one or more halogens.

6. The indane compound according to claim 1 or a pharmaceutically acceptable salt or solvate thereof, wherein X$^1$-X$^4$ are CH.

7. The indane compound according to claim 1 or a pharmaceutically acceptable salt or solvate thereof, wherein L$^1$ is CH$_2$.

8. The indane compound according to claim 1 or a pharmaceutically acceptable salt or solvate thereof, wherein L$^1$ is O.

9. The indane compound according to claim 1 or a pharmaceutically acceptable salt or solvate thereof, wherein R$^{23}$ and R$^{24}$ are independently H or C$_{1-4}$alkyl.

10. The indane compound according to claim 1 or a pharmaceutically acceptable salt or solvate thereof, wherein Y$^1$-Y$^3$ are CH.

11. The indane compound according to claim 1 or a pharmaceutically acceptable salt or solvate thereof, wherein L$^2$ is NHSO$_2$.

12. An indane compound according to claim 1 selected from:

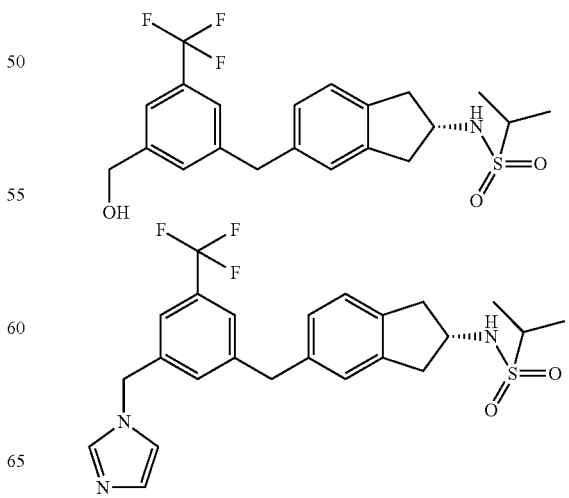

65
-continued
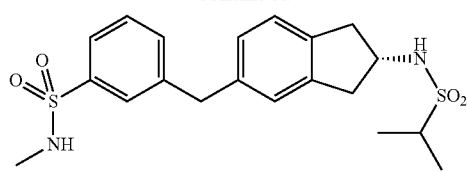
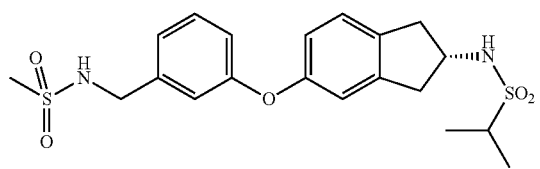
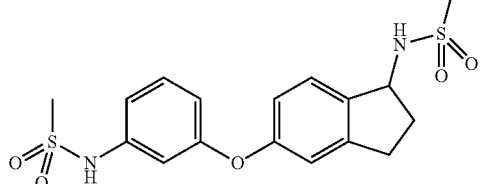
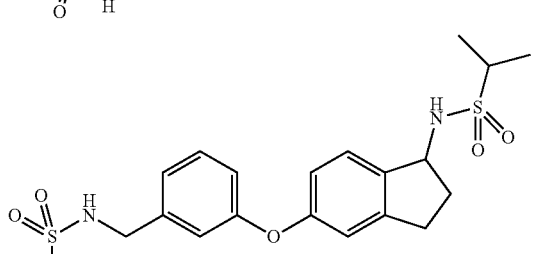
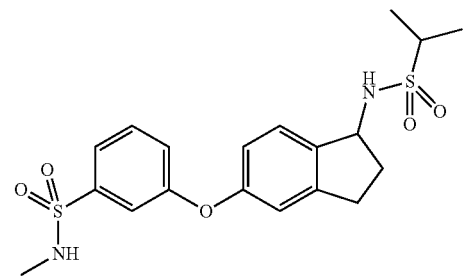
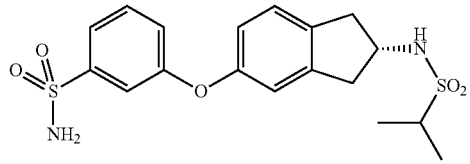
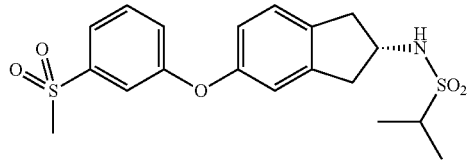
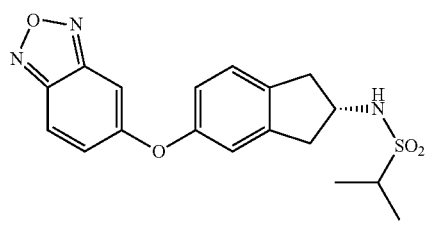
66
-continued
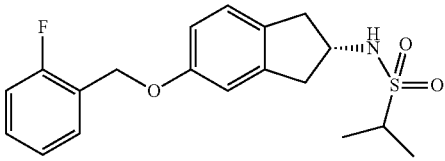
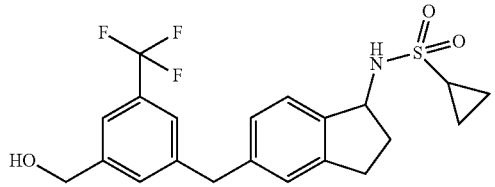
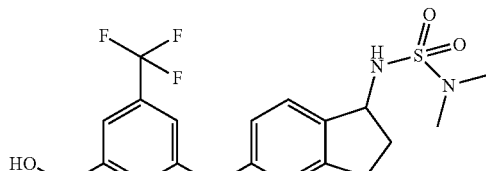
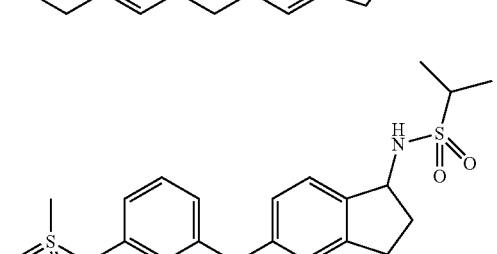
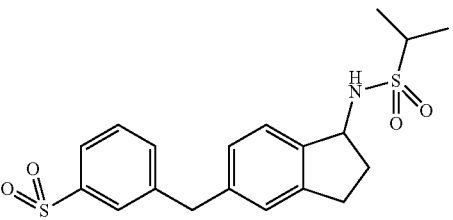
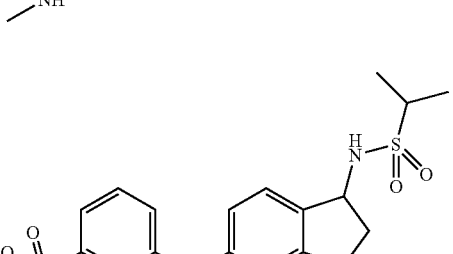
and -continued

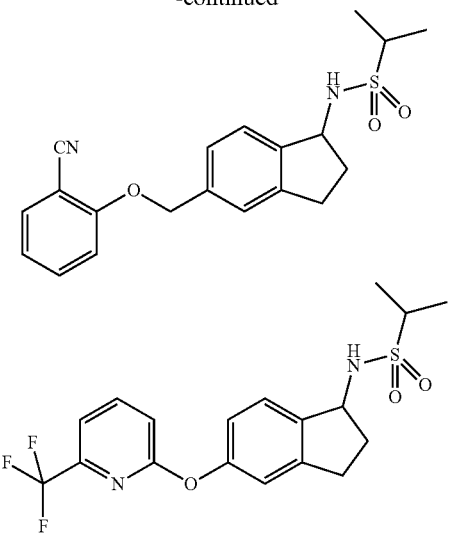

or a pharmaceutically acceptable salt or solvate thereof.

13. A method for treating psychiatric diseases wherein an enhancement of synaptic responses mediated by AMPA receptors is required, the method comprising administering a therapeutically effective amount of an indane compound according to claim 1 or a pharmaceutically acceptable salt thereof.

14. A method for treating psychiatric diseases wherein an enhancement of synaptic responses mediated by AMPA receptors is required, the method comprising administering a therapeutically effective amount of an indane compound according to claim 12 or a pharmaceutically acceptable salt thereof.

15. A pharmaceutical composition comprising an indane compound according to claim 1 or a pharmaceutically acceptable salt thereof in admixture with one or more pharmaceutically acceptable auxiliaries.

16. A pharmaceutical composition comprising an indane compound according to claim 12 or a pharmaceutically acceptable salt thereof in admixture with one or more pharmaceutically acceptable auxiliaries.

\* \* \* \* \*